(12) United States Patent
Montgomery et al.

(10) Patent No.: US 10,365,261 B2
(45) Date of Patent: Jul. 30, 2019

(54) SYSTEM AND METHOD FOR DETERMINING STRATIGRAPHIC LOCATION AND AREAL EXTENT OF TOTAL ORGANIC CARBON USING AN INTEGRATED STRATIGRAPHIC APPROACH

(71) Applicant: Chevron U.S.A. Inc., San Ramon, CA (US)

(72) Inventors: Paul Montgomery, Kingswells (GB); Kenneth Ratcliffe, Powys (GB); Chris Richard Bell, Scotland (GB); Robert Locklair, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 248 days.

(21) Appl. No.: 14/802,254

(22) Filed: Jul. 17, 2015

(65) Prior Publication Data
US 2016/0018556 A1    Jan. 21, 2016

Related U.S. Application Data

(60) Provisional application No. 62/026,347, filed on Jul. 18, 2014.

(51) Int. Cl.
G01N 33/24    (2006.01)
(52) U.S. Cl.
CPC ....... *G01N 33/24* (2013.01); *G01N 2033/243* (2013.01)
(58) Field of Classification Search
None
See application file for complete search history.

(56) References Cited

U.S. PATENT DOCUMENTS

| 9,495,488 B2 * | 11/2016 | Jones | G06F 17/5009 |
| 2010/0057409 A1 * | 3/2010 | Jones | G01N 33/24 |
| | | | 703/2 |
| 2014/0297186 A1 * | 10/2014 | Suarez-Rivera | G01B 21/20 |
| | | | 702/2 |

OTHER PUBLICATIONS

Sageman et al.; "A tale of shales: the relative roles of production, decomposition, and dilution in the accumulation of organic-rich strata, Middle-Upper Devonian, Appalachian basin"; Chemical Geology 195; 2003; pp. 229-273.

(Continued)

*Primary Examiner* — Reema Patel
*Assistant Examiner* — Steven M Christopher
(74) *Attorney, Agent, or Firm* — Mary R. Bram; Melissa M. Hayworth; Marie L. Clapp

(57) ABSTRACT

An integrated stratigraphic method for determining total organic carbon (TOC) in a rock formation is provided, The method includes performing a geochemical analysis method to create a geochemical dataset; performing a chronostratigraphic method to create a chronostratigraphic dataset; performing a graphic correlation of the chronostratigaphic dataset from at least one location in the rock formation; determining a sequence stratigraphic model based on the graphic correlation; and generating a palaeogeographic reconstruction at one or more time periods by integrating the sequence stratigraphic model with the geochemical dataset to construct a predictive depositional model and determine a location and areal extent of total organic carbon within the rock formation.

31 Claims, 18 Drawing Sheets

(56) References Cited

OTHER PUBLICATIONS

International Search Report and Written Opinion dated Oct. 27, 2015 for Appln. No. PCT/US2015/040958.
Mubarak Matlak Al-Hajeri et al: "Basin and Petroleum System Modeling", Oilfield Review Summer 2009, Jun. 21, 2009 (Jun. 21, 2009), pp. 14-29, XP055066532, Retrieved from the Internet: URL:http://www.slb.com/~/media/Files/resources/oilfield_review/ors09/sum09/basin_petroleum.ashx[retrieved on Jun. 13, 2013].
Austin Taylor Luker: "A Comparison of Sequence Stratigraphy and Mineralogical Variations Associated With Total Organic Carbon in the Marcellus Formation: Washington County, Pennsylvania", Dec. 1, 2012 (Dec. 1, 2012), XP055217360, Retrieved from the Internet: URL:https://repositories.tdl.org/uh-ir/bitstream/handle/10657/455/Luker_Thesis_Finai_NSM1.pdf?sequence=1 [retrieved on Sep. 30, 2015].
Suarez-Ruiz, et al., "Review and update of the applications of organic petrology: Part 1, geological applications", International Journal of Coal Geology 99 (2012), pp. 54-112.
Youngquist, Walter, "Shale Oil—The Elusive Energy," Hubbert Center Newsletter # 98/4. Colorado School of Mines, Oct. 1998, 8 pages.
STRATA Terminology, "Chronostratigraphic correlation chart", http://www.sepmstrata.org/Terminology.aspx?d=chronostratigraphic%20correlation%20chart, accessed Jul. 10, 2018, 1 page.
Introduction to Sequence Stratigraphy—SEPM Strata, http://www.sepmstrata.org/page.aspx?pageid=15, accessed Jul. 10, 2018, 6 pages.

* cited by examiner

SYSTEM AND METHOD FOR DETERMINING STRATIGRAPHIC LOCATION AND AREAL EXTENT OF TOTAL ORGANIC CARBON USING AN INTEGRATED STRATIGRAPHIC APPROACH

CROSS REFERENCE TO RELATED APPLICATIONS

The present application claims the benefit of U.S. Provisional Patent Application No. 62/026,347, filed on Jul. 18, 2014, the entire content of which is incorporated herein by reference.

FIELD

The present invention relates to a system and method for determining the stratigraphic location and areal extent of total organic carbon using an integrated stratigraphic approach.

BACKGROUND

Three fundamental processes regulate burial and preservation of organic matter in the sedimentary record and thus of organic carbon. These processes are dilution, production and decomposition. The impact of these processes can be modified by the rate at which they occur.

Rocks, via outcrop, cores, core chips, plugs, cuttings, or other, can be analyzed by geochemical methods to determine the geochemistry and hydrocarbon potential in rock formations or units of interest. The rocks, cores, cutting, core chips, etc. can be further studied using stratigraphic methods to determine a history of deposition of sediments (stratigraphic sequence). The geochemical methods and the stratigraphic methods can be used together to evaluate the likely presence and concentration of total organic carbon and its mode of deposition within a basin. Conventional methods have used each of the geochemical and stratigraphy methodologies independently. However, each method alone provides only a limited insight as to how or where potential organic carbon is present in the rock formation of interest.

The following paragraphs describe an integrated stratigraphic methodology that incorporates both the geochemical methods and the stratigraphic methods and the inter-dependencies between them, thereby allowing the construction of depositional models through geologic time that provide a more complete insight as to how and/or where potential organic carbon rich sediments will have accumulated within a hydrocarbon basin.

SUMMARY

An aspect of the present invention is to provide an integrated stratigraphic method for determining total organic carbon (TOC) in a rock formation. The method includes performing a geochemical analysis method to create a geochemical dataset, the geochemical analysis method comprising at least one of: (a) performing a production analysis on a sample extracted from the rock formation; (b) determining an amount of dilution in the rock formation; or (c) performing a redox analysis on the sample extracted from the rock formation. The method further includes performing a chronostratigraphic method to create a chronostratigraphic dataset, the chronostratigraphic method comprising at least one of: (1) performing a paramagnetic (PMAG) procedure using a magnetic measuring device to measure changes in direction of magnetism in the rock formation; (2) performing a biostratigraphy procedure to determine time or age of deposition of sediment using flora or fauna dating, or both, if fauna or flora, or both, is found in the rock formation; (3) performing a bentonite analysis procedure; (4) performing a cyclostratigraphy procedure; or (5) performing a Rhenium-Osmium (Re—OS) chronology procedure if an amount of total organic carbon (TOC) or Pyrite determined using the geochemical analysis method is equal to or greater than approximately 1.5%; and measuring changes in preserved organic carbon $\delta^{13}C_{org}$ or changes in dissolved inorganic carbon $\delta^{13}C_{carb}$, or both, to recognize global changes in the oceanic dissolved inorganic carbon. The method further includes performing a graphic correlation of the chronostratigaphic dataset from at least one location in the rock formation; determining a sequence stratigraphic model based on the graphic correlation; and generating a palaeogeographic reconstruction at one or more time periods by integrating the sequence stratigraphic model with the geochemical dataset to construct a predictive depositional model and determine a location and areal extent of total organic carbon within the rock formation.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various Figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
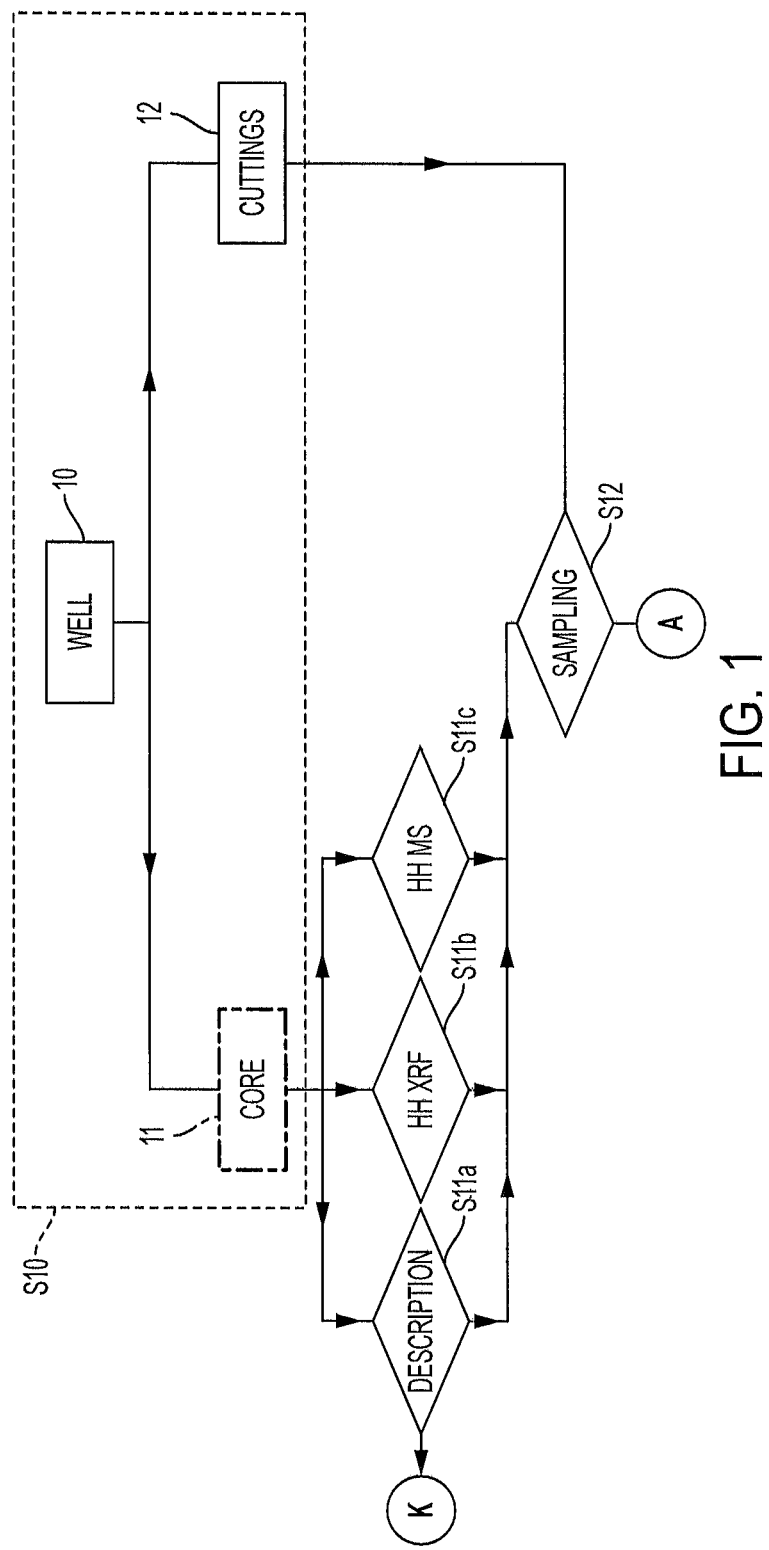
FIG. 1 depicts a flow chart of a screening portion of a method for integrated stratigraphic method for creating a depositional model, according to an embodiment of the present invention.

FIG. 1 depicts a flow chart of the screening portion of an integrated stratigraphic method for constructing a depositional model, according to an embodiment of the present invention. The integrated stratigraphic method includes collecting raw material at S10. For example, the raw material can be collected from a well 10 as one or more cores 11 (e.g., conventional cores, sidewall cores), as one or more cuttings 12, or both. Although cores are provided herein as examples, other types of samples can also be used including, plugs or chips, etc. In the case of the collected one or more cores 11, a set of evaluation or screening procedures are performed to the one or more cores 11. For example, the evaluation procedures include describing the one or more cores 11 with the naked eye under natural light or under ultraviolet light, at S11a, or any combination of these procedures. The evaluation or screening procedures may further include measuring X-Ray fluorescence of the one or more cores 11 using a Hand Held X-Ray Fluorescence (HHXRF) device, at S11b, and/or measuring the magnetic susceptibility of the one or more cores 11 using a Hand Held Magnetic Susceptibility (HHMS) device, at S11c. These evaluations or screening procedures S11a, S11b and/or S11c can provide information or direction on how many times and where in the one or more cores additional samples for further evaluation are best collected from, as will be described in the following paragraphs. Although it may be referred to core(s) or cutting(s) in the plural form in the following paragraphs, this should not however be read as to be limited to a plurality but can encompass one or more cores or one or more cuttings.

In the case of cuttings 12, the cuttings samples are produced from the drilling action and fluid circulation in well-bores and are collected to represent composited intervals that can be 1 m, 3 m or 5 m thick. Each composited cuttings sample are is labeled with two depths that provide the depth interval in the well-bore that the composited cuttings sample represents. In some instances, the cuttings are referred to as "spot cuttings", which means that the chips produced by drilling represent a single layer of rock. These cuttings are labelled with a single value that indicates the depth in the well bore the cuttings sample represents.

The method further includes performing a sampling procedure S12 on the one or more cores 11 and/or cuttings 12, For example, the sampling procedure at S12 may include isolation of specific chips of rock from the one or more cuttings 12. This may include sampling of the one or more cores 11 by extracting plugs or other samples from the one or more cores at specific depths. The location of the extraction of sample material (e.g., plugs) from core 11 is selected according to the information collected using the evaluation procedures S11a (Physical Description), S11b (HHXRF testing), or S11c (HHMS testing), or any combination of two or more of these procedures.

For example, if 100 meters of core are collected, the evaluation or screening procedure can allow the specialist (e.g., geologist) to select the location of samples in the 100 m of core (e.g., sampling every 1 meters or 2 meters). In other words, these screening or evaluation procedures can direct the geologist to an area in the collected core or in the un-cored well-bore where more detailed geochemical analysis may be desired. The position on the core or cutting where the sample is extracted or collected is noted and thus is known. Consequently, the location and depth in a rock formation from which the sample originated is also known. The method progresses as depicted by the symbol "A" to undergo a geochemical analysis method ("Geochemical Workflow") to create a geochemical dataset and a chronostratigraphic method ("Chronostratigraphic Workflow") to create a chronostratigraphic dataset, as will be described in detail in the following paragraphs.

Figure 2:
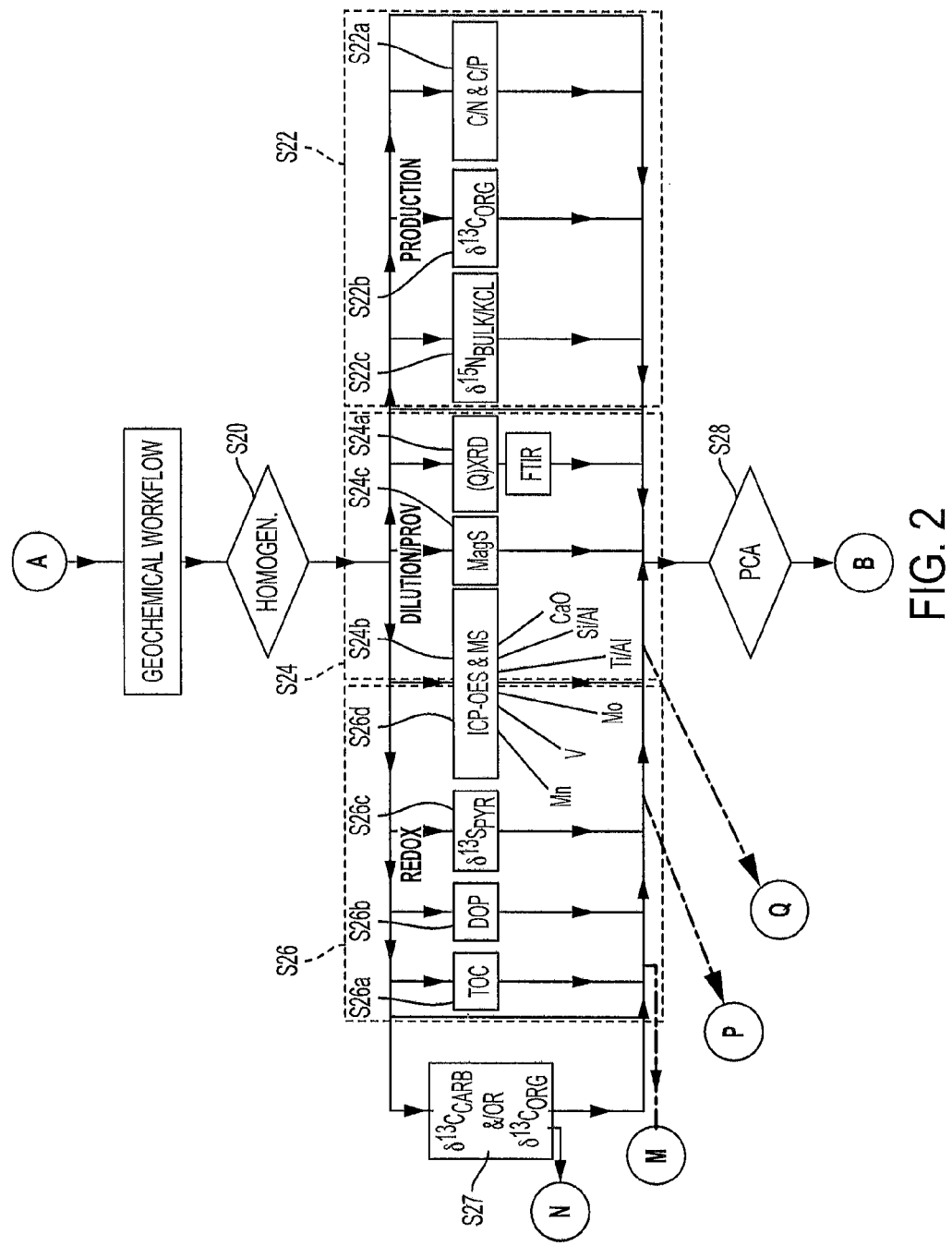
FIG. 2 depicts a flow chart of a geochemical analysis method, according to an embodiment of the invention.

FIG. 2 depicts a flow chart of a geochemical analysis method to create a geochemical dataset, according to an embodiment of the invention. The geochemical analysis method is part of the overall method for integrated stratigraphic method or framework for creating the depositional model. The geochemical analysis method includes homogenizing the samples collected from the one or more cores and/or the one or more cuttings, at S20. In one embodiment, the homogenization is performed using a riffle box splitter. For example, the samples in the form of powder or gravel are run through the riffle box which shakes and splits the samples into a plurality of approximately equal portions. The portion of the sample at the bottom of the splitter is rerun again through the riffle box splitter and split into a plurality of portions. This process is repeated until the required number of aliquots is obtained. The number of aliquots is determined by the number of tests that will be performed on the homogenized samples. The geochemical analysis method includes performing a production ('palaeo-productivity') analysis, at S22, performing dilution ('sediment dilution') analysis, at S24, and performing a redox ('palaeo-redox') analysis at S26.

Figure 7:
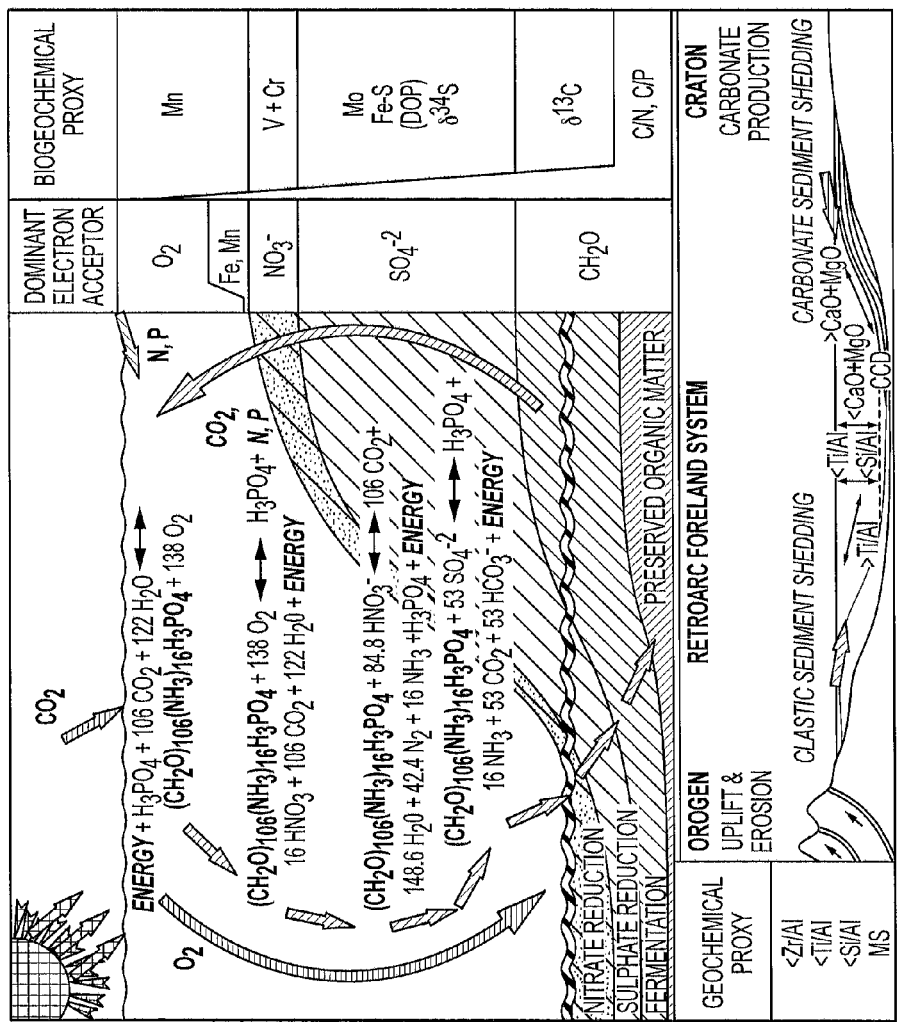
FIG. 7 is a schematic diagram showing the processes involved in organic matter incorporation and preservation, according to an embodiment of the present invention.

In one embodiment, performing a palaeo-productivity or production analysis, at S22, includes determining the presence and proportion of certain elements that are occurring in the basin where the sediments accumulated and that relate to palaeo-productivity. FIG. 7 is schematic diagram showing the processes involved in organic matter incorporation and preservation, according to an embodiment of the present invention. FIG. 7 illustrates various processes or mechanisms for incorporating various elements (e.g., Carbon, Nitrogen, Phosphorous, etc.) into a sedimentary accumulation layer. In one embodiment, determining the proportion of the elements within the sediments includes, for example, measuring carbon to nitrogen (C/N) ratio, and/or carbon to phosphorus (C/P) ratio, etc., at S22a, measuring the stable carbon isotope ($\delta^{13}C_{org}$) of organic matter in sediment, at S22b, or measuring the stable nitrogen isotope in the sediments (e.g., $\delta^{15}N_{bulk/KCL}$), at S22c, or any combination thereof. Each of these measurements at S22a, S22b and S22c can be used to address various aspects of primary drivers behind the deposition of the organic material (e.g., preserved organic matter illustrated in FIG. 7).

In one embodiment, performing the 'sediment dilution' analysis, at S24, includes determining an amount of dilution of the organic material and the diluting mineral or combination of minerals. In one embodiment, determining the amount of dilution includes using quantitative X-Ray diffraction (QXRD) by employing an X-Ray diffraction apparatus, at S24a, to identify the diluting minerals, which can include quartz and calcite and to determine their abundances. Another method for determining sediment dilution is the application of Fourier Transform Infrared (FTIR) analysis on samples by using an FTIR apparatus. The FTIR technique is an efficient and rapid method for determining sediment dilution. However, the FTIR analysis uses QXRD data in order to "train" a FTIR software (e.g., QUANT by PerkinElmer Corporation). Once this training has been carried out, the FTIR technique is able to quickly determine sediment dilution parameters on all samples.

Figure 16:
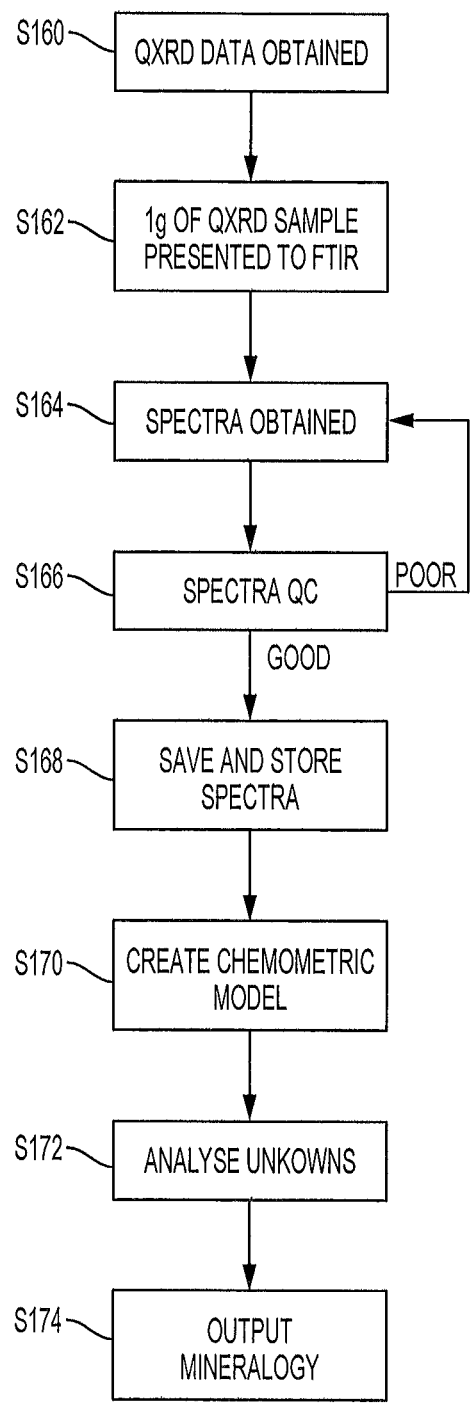
FIG. 16 depicts a flow chart of an example of a process using QXRD along with FTIR to determine an amount of dilution of sediments, according to an embodiment of the present invention.

FIG. 16 depicts a flow chart of an example of a process using QXRD along with FTIR to determine an amount of dilution of sediments, according to an embodiment of the present invention. As shown in FIG. 16, QXRD data are acquired (at S24a) on select rock samples to quantify diluting minerals, at S160. The rock sample from which those data were acquired is subsequently homogenized and an aliquot (e.g., 1 g aliquot) is separated. The aliquot is presented to the FTIR instrument in powder form, at S162. Infrared (IR) spectra are obtained, at S164, from each QXRD sample analyzed, at S24a. Following quality control (QC) of those spectra, at S166, the samples are processed using off the shelf software (e.g., QUANT by PerkinElmer Corporation) together with quantified mineralogy using off the shelf software (e.g., QUANT by PerkinElmer Corporation), at S168, to create a chemometric model, at S170. By obtaining IR spectra on unknown samples, at S172, and processing them through the chemometric model, bulk mineralogy of a similar nature to that obtained using QXRD can be obtained, at S174. The processing time for unknown samples using FTIR (e.g., Attenuated Total Reflectance ATR-FTIR) is sufficiently fast that large and statistically defendable dilution models can be acquired.

Figure 15A:
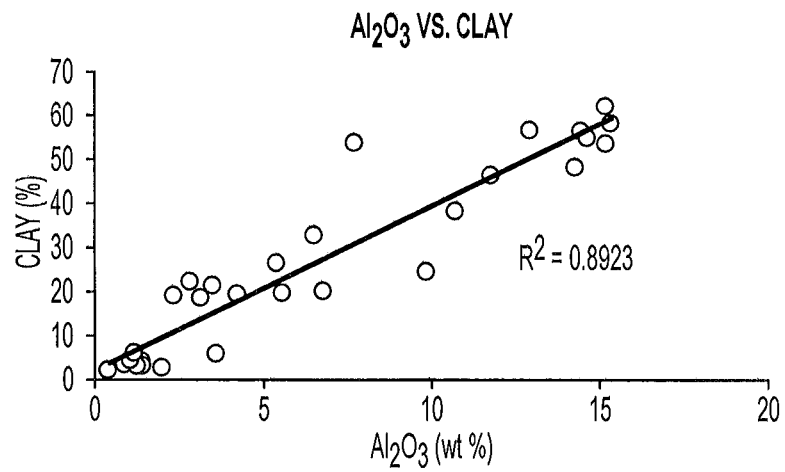
FIGS. 15A and 15B are cross plots of selected elemental data from inductively coupled plasma optical emission spectroscopy (ICP-OES) and mass spectrometry (MS) analysis and mineralogical data from quantitative X-Ray diffraction (QXRD) showing the manner in which elemental data can be used as mineralogical proxies in order to help understand dilution.
Figure 15B:
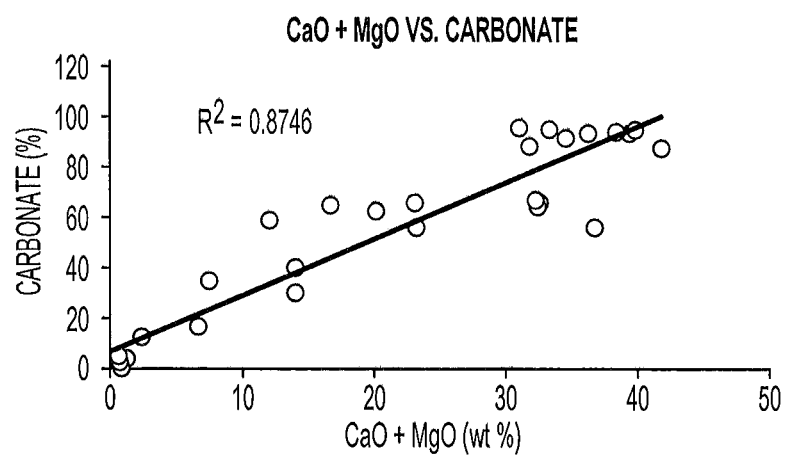

Determining the amount of dilution at S24 may also include using inductively coupled plasma optical emission spectroscopy by employing an inductively coupled plasma optical emission spectrometer and mass spectrometry by employing a mass spectrometer (ICP-OES & MS), at S24b, to study elemental concentrations in rock material. One efficient way to obtain a measure of dilution is by adopting elemental proxies that represent minerals (a proxy relationship between elemental proxies and minerals). The proxy relationship can be established via cross correlation of ICP-OES & MS with QXRD data. FIGS. 15A and 15B are cross plots of selected elemental data from inductively coupled plasma optical emission spectroscopy (ICP-OES) and mass spectrometry (MS) analysis and mineralogical data from quantitative X-Ray diffraction (QXRD) showing the manner in which elemental data can be used as mineralogical proxies in order to help understand dilution. The elemental data from ICP OES & MS are termed chemostratigraphic and can be based on element ratios, such as, for example, Si/Al, Ti/Al, etc., that provide information on sediment grain-size variations. Chemostratigraphic data can also provide information about where the sediment was derived from (using, for example, Zr and Cr concentrations), and provide information about the climate during deposition of the sediments (using elements such as Al, Ga and Rb). Various combinations of elements and elements ratios can be used to define detailed lithostratigraphic correlation.

In one embodiment, determining the amount of dilution may also include using magnetic susceptibility (MagS) by employing a magnetic susceptibility measuring apparatus, at S24c. MagS is a method that provides data that can be indicative of terrigenous input, erosion—deposition cycles, climatic cycles, which in addition to providing indication of dilution can be used to aid with sequence stratigraphic modeling (sequence stratigraphic model).

In one embodiment, performing the redox analysis, at S26, includes determining the redox conditions of the sediments at the time of accumulation and the oxygenation state of the water column in which those sediments have accumulated. In one embodiment, determining conditions of sediments and the water column includes determining proxies that provide information about oxic and anoxic conditions of the water column and the deposited sediments. Determining conditions includes measuring the total preserved organic content in sediment (TOC), at S26a, measuring the degree of pyritization (DOP), which is the ratio of pyrite iron to the sum of pyrite iron and reactive iron that can be related to the depositional environment in sediments, at S26b, or measuring Sulfur isotopes ($\delta^{34}S_{pyr}$) of pyrite to estimate the oxygenation state of palaeo-water column conditions at the time of deposition, at S26c, or any combination thereof.

Figure 8:
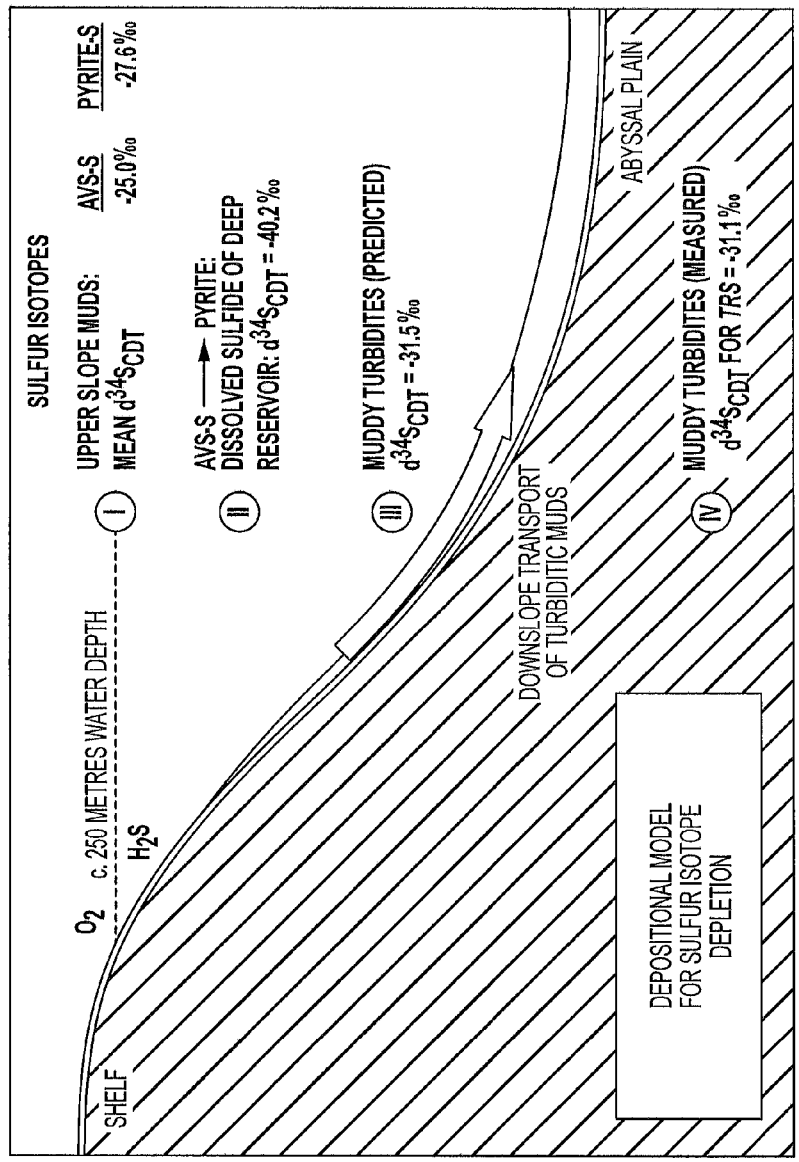
FIG. 8 is a schematic diagram showing a depositional model for sulfur isotope depletion, according to an embodiment of the present invention.

FIG. 8 is a schematic diagram showing a depositional model for sulfur isotope depletion, according to an embodiment of the present invention. The sulfur isotope values become more negative as anoxia increases (decrease in oxygen levels) and reach a minimum when the water column experiences prolonged euxinic conditions. During these prolonged periods of anoxia, pyrite is precipitated in the water column and settles out on the basin floor. Mixing of turbiditic sediment from the basin shelves can increase the sulfur isotope values so they become slightly less negative and this can be used to indicate the approximate location of the sediment within the basin, i.e., basin floor or basin slope.

The whole rock elemental composition of ancient sediments also provides information on the redox state of the sediments at the time of deposition. Therefore, aspects of the ICP OES & MS data such as concentrations of elements Mn, Mo, V, etc. collected at S24b provide information on the redox state of the sediments (FIG. 7).

By combining the different geochemical analysis methods described above and shown in FIG. 2, an understanding of what the productivity, sedimentary redox, water column redox and the main diluting factors were at the time of deposition in the location where the core, cuttings, core chips were collected can be achieved.

In addition to performing the above described 'palaeo-productivity' analysis method, at S22, the dilution analysis method, at S24 and the redox analysis method at S26, the global preservation of organic matter in sediment using carbon isotopes ($\delta^{13}C_{carb}$ and/or $\delta^{13}C_{org}$) can also be evaluated, at S27. The term $\delta^{13}C_{carb}$ reflects changes in dissolved inorganic carbon (DIC) whereas the term $\delta^{13}C_{org}$ reflects changes in preserved organic carbon (OC), both of which are controlled by the global carbon cycle. $\delta^{13}C_{carb}$ has average value of approximately 0‰ whereas $\delta^{13}C_{org}$ has average value of approximately −25‰, the 25‰ offset results from kinetic fractionation during photosynthesis. Both variables can indicate primary productivity and burial rates but can be influenced by different factors. Under normal circumstances, both are correlative and in parallel because there is no change to isotopic fractionation (FIG. 7 and FIG. 9).

Figure 9:
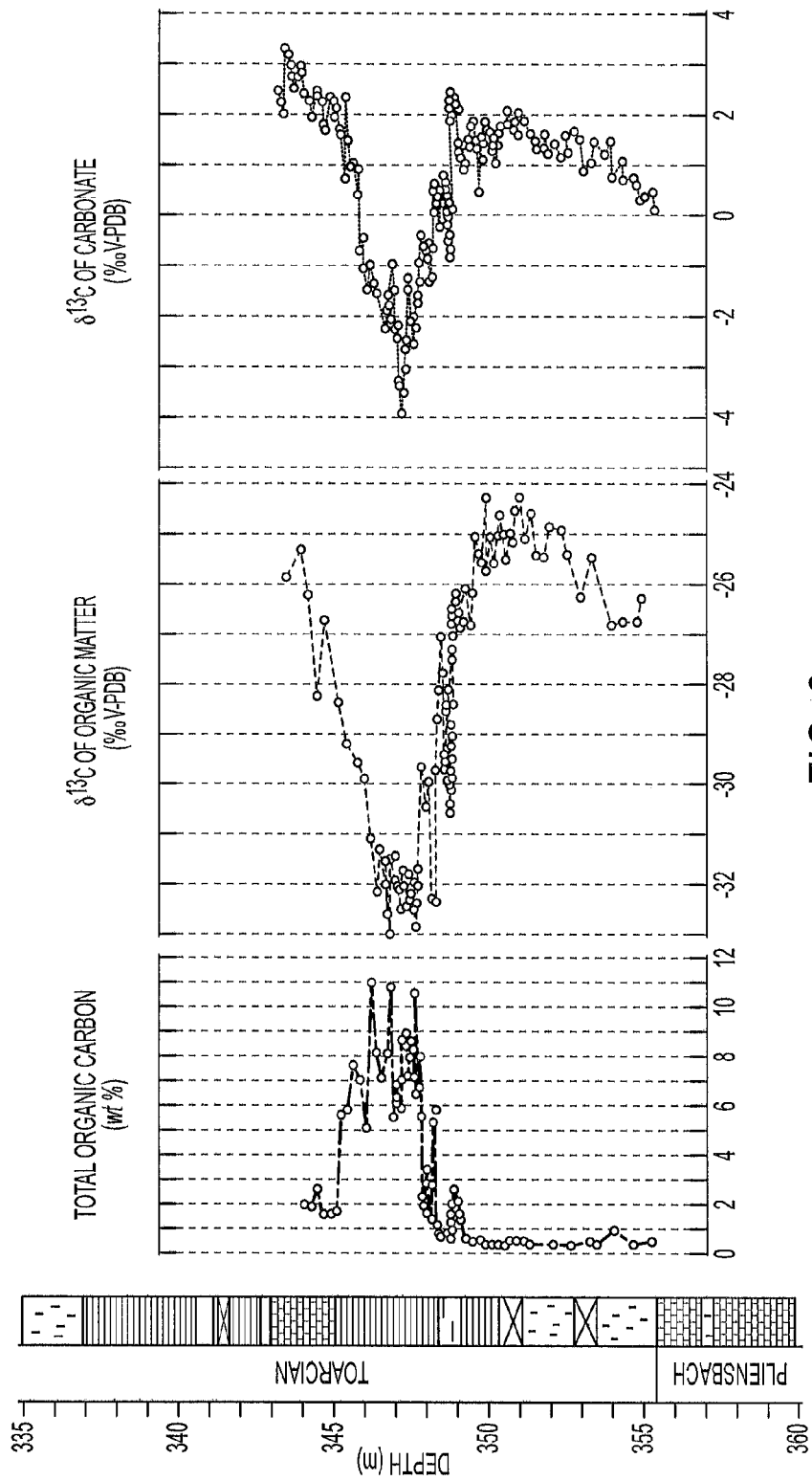
FIG. 9 are plots of concentration of carbon from organic matter and carbon from carbonate and the total organic carbon (TOC) as a function of depth, showing the relationship between TOC, $\delta^{13}C_{org}$ and $\delta^{13}C_{carb}$, according to an embodiment of the present invention.

FIG. 9 depicts plots of $\delta^{13}C_{org}$ (measured from organic carbon), $\delta^{13}C_{carb}$ (measured from carbonate carbon) and the total organic carbon (TOC) as a function of depth in a well bore, according to an embodiment of the present invention. These plots show the relationship between TOC, $\delta^{13}C_{org}$ (organic carbon) and $\delta^{13}C_{carb}$ (inorganic carbon). Since these two variables $\delta^{13}C_{org}$ (organic carbon) and $\delta^{13}C_{carb}$ (inorganic carbon) reflect global changes influenced by the carbon cycle, changes in their values within a sediment will provide a means to define global and local chronostratigraphic correlations, which are described in the below paragraphs, as part of the chronostratigraphic workflow.

Figure 10:
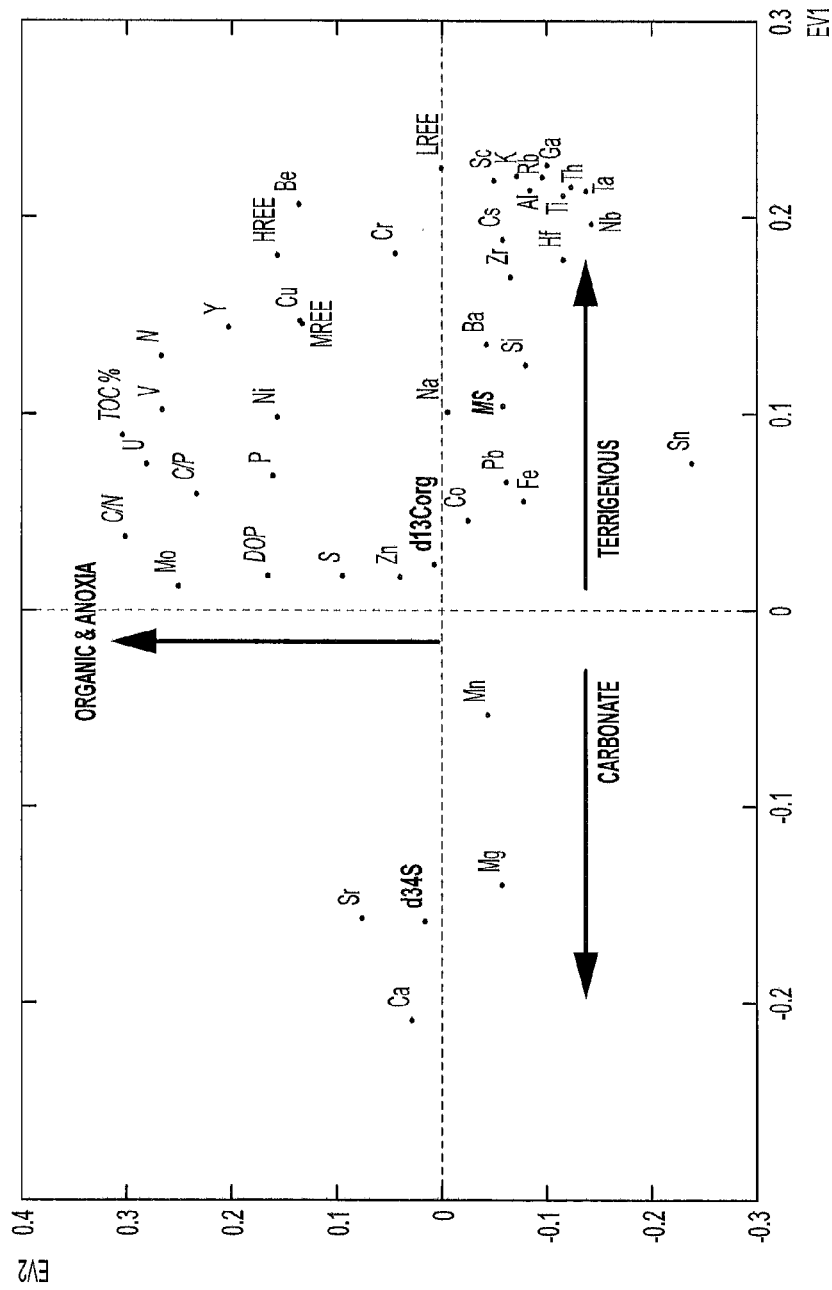
FIG. 10 is a plot that is obtained using principal component analysis (PCA) showing interdependency of the data acquired in some aspects of geochemical workflow, according to an embodiment of the present invention.

Many of the variables collected in the geochemical workflow have complex associations in sediments and frequently reflect markedly different processes in different locations and conditions. For any given sediment, knowing which variables can best be used to recognize palaeo-productivity, dilution (and/or provenance) and palaeo-redox conditions can provide better results when using the present integrated stratigraphic method. The method includes using the collected data in a multivariate statistical principal component analysis (PCA) software program, at S28, so as to determine which of the various geochemical proxies show associations (FIG. 10). PCA can be seen as exploratory data analysis process to identify geochemical associations in order to form predictive models. The geochemical associations for high TOC mudrocks deposited at different times in geological history and in different basins around the world will vary.

FIG. 10 is a plot that is obtained using principal components analysis (PCA) showing interdependency of the data acquired in some aspects of geochemical workflow, according to an embodiment of the present invention. The value for each principal component is calculate from the component Eigenvectors (EV), whereby principal component 1 accounts for the largest amount of variability in the dataset, principal component 2 the second largest amount of variability, principal component 3, the next largest amount of variability and so on until all variability in the original dataset is accounted for. Each variable determined in the processes described above will have a unique EV value for each principal component. Ideally EV should be viewed in multi-dimensional space, but for practical reasons to EV's are cross-plotted in two dimensions. On FIG. 10, the more closely two variables plot to one another, the more closely they are associated in the sediments from which the data were collected. For example the ICP OES-MS derived chemostratigraphic elements Molybdenum (Mo), Vanadium (V), and Uranium (U) plot are in close association to one another and TOC on FIG. 10, which indicates that these elements are all associated with organic carbon.

Figure 11:
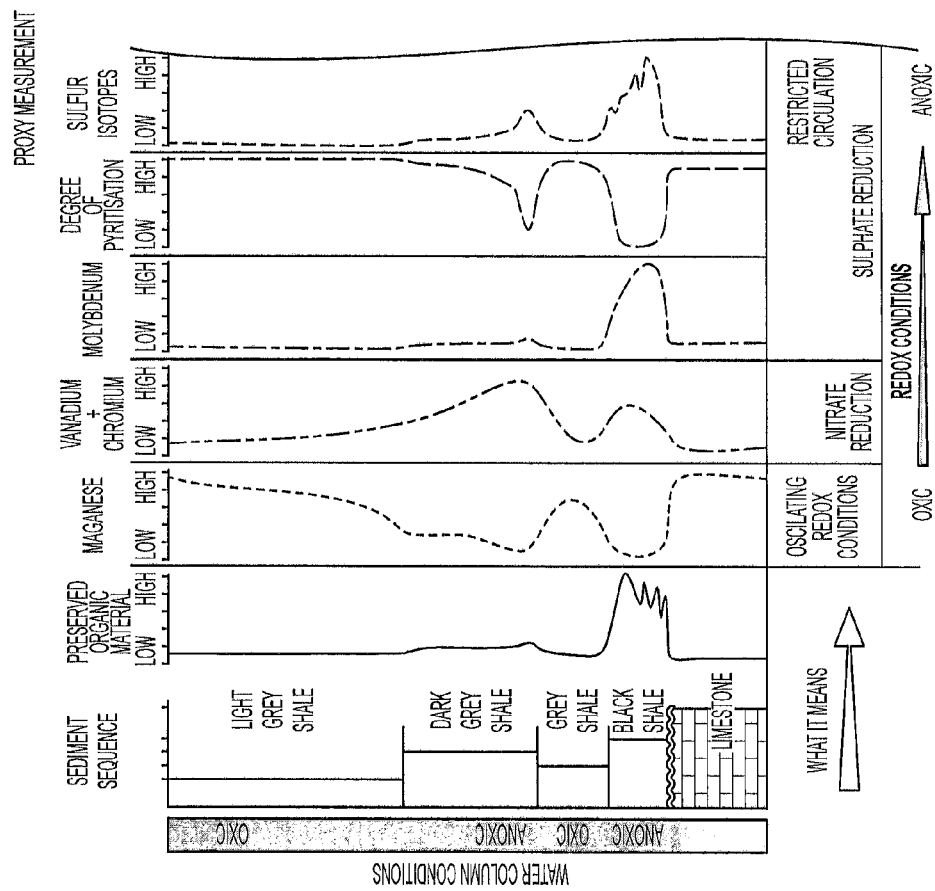
FIG. 11 shows plots of concentration of various elements for a relatively high total organic carbon shale content from one basin, according to an embodiment of the present invention.
Figure 11:
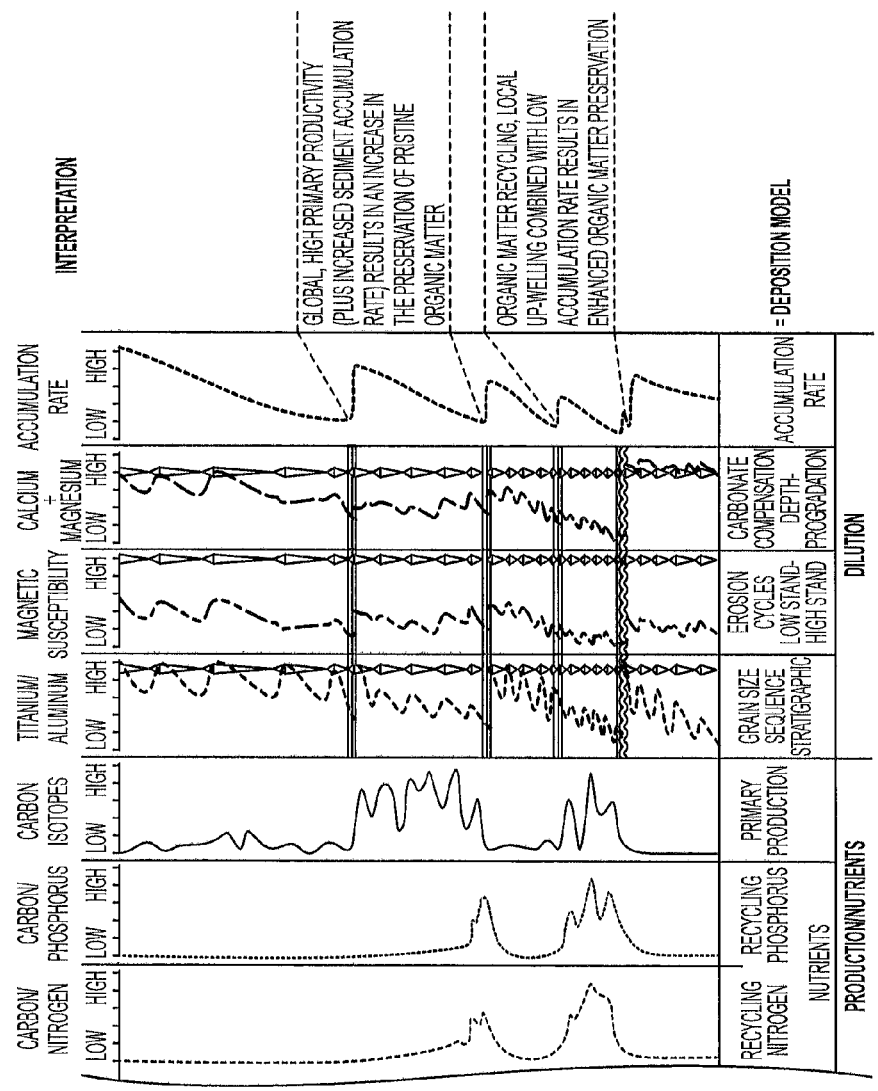

FIG. 11 shows plots of concentration of various elements for high total organic carbon (TOC) shale content from one basin, according to an embodiment of the present invention. FIG. 11 is representative of an example output from findings from one location after performing the sampling depicted in FIG. 1 and TOC analysis at S26a as part of the Geochemical Workflow depicted in FIG. 2.

After performing the PCA analysis at S28, the geochemical analysis method (Geochemical Workflow) ends at point "B", as shown in FIG. 2.

Figure 3:
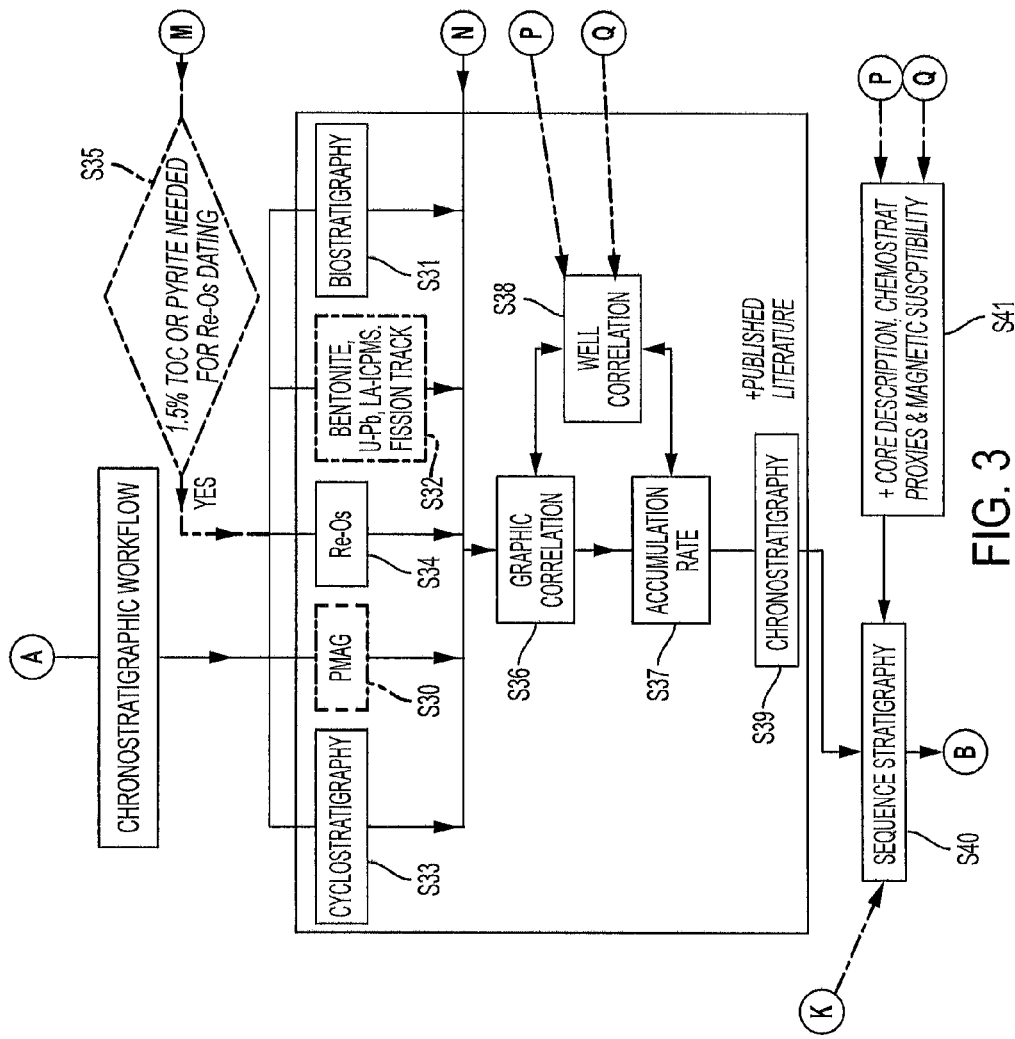
FIG. 3 depicts a flow chart of chronostratigraphic analysis method, according to an embodiment of the invention.

As stated above, the integrated stratigraphic method also progresses to point "A" to include performing the chronostratigraphic analysis method ("Chronostratigraphic Workflow") to create a chronostratigraphic dataset. FIG. 3 depicts a flow chart of chronostratigraphic analysis method, according to an embodiment of the invention. The chronostratigraphic analysis method is complementary to the geochemical analysis method and includes using some of data in the Geochemical Workflow as part of the Chronostratigraphic Workflow. For example the data collected at S22b and S27 ($\delta^{13}C_{org}$ and/or $\delta^{13}C_{carb}$) in the Geochemical Workflow can be used in the Chronostratigraphic Workflow (FIG. 3), as shown at point "N".

In one embodiment, the chronostratigraphic analysis method provides information about accumulation history of sediments or strata via the determination of the absolute time of deposition of the sediments being considered. For example, the chronostratigraphic analysis method provides the time that elapsed between a depositional layer at one location in a well bore and another depositional layer at another location in the well bore by analyzing a core or cutting. The chronostratigraphic method includes a series of procedures that may be used in various combinations to establish a relationship between the samples collected from the one or more cores or collected from the one or more cuttings and geologic time.

The chronostratigraphic method includes performing a palaeomagnetic (PMAG) procedure using a magnetic measuring device, at S30. The PMAG procedure is carried out on plugs taken from conventional core 11. In one embodiment, the plugs may be extracted at the same location as the homogenized samples for the geochemical analysis so as to link the palaeomagnetic (PMAG) analysis with the geochemical analysis. However, the plugs may also be extracted at different locations. The plugs are then step-wise demagnetized (using increasing temperatures or alternating fields) to remove any magnetic components that were acquired by the sediment in its history from deposition, through burial and potentially through uplift to its present day location. The magnetic field that is most stable (or hardest to remove) is typically the one that records the earth's magnetic field direction when the sediment from which the plug was extracted was deposited. The earth's magnetic field direction has changed during geological history in a binary manner. The magnetic field direction is either pointed up towards the north (referred to as "normal polarity"), or pointed down towards the south (referred to as "reversed polarity"). This binary magnetic signal (normal or reversed) that represents the earth's magnetic field is recorded from the stratigraphically located plugs extracted from the cores. The record of changes over geologic time of the Earth's magnetic field are well known in published records thereby allowing the reversed and normal polarities extracted from core plugs to be correlated with geological time. Hence, by measuring the direction of the polarity through a core by extraction of plugs and demagnetization, it is possible to determine the time elapsed between layers.

The order of performing the geochemical analysis and the PMAG analysis is not important. However, for efficiency purposes, it may be beneficial to first perform the PMAG analysis, at S30. In this way, the same plugs that are used to perform the PMAG analysis can be transformed into gravel or powder form and homogenized, at S20 to perform the geochemical analysis described in the above paragraphs. However, in some instances, if PMAG, at S30, is not used as a dating method, then plugging may not be needed. In which case samples are simply transformed or extracted into powder or gravel form to perform the geochemical analysis.

Other procedures that can be used to link time with a position of the sample extracted from the core or cutting include performing a biostratigraphy procedure, at S31. Biostratigraphy includes the study of the fauna or flora, or both, within the core or cuttings. Since the time period that certain fauna or flora lived is known, the time information can be obtained from the observation fauna and flora in the sample extracted from the core or cuttings.

Another procedure that can be used to link time with a position of the sample extracted from the core include performing a Bentonite analysis including performing a U—Pb (Uranium-Lead), LA-ICPMS (Laser Ablation Inductively Coupled Plasma Mass Spectrometry) or U—Pb fission track analysis, or any combination thereof, on zircons crystals within bentonites, at S32. Bentonites are layers of volcanic ash incorporated into the sedimentary layers. They contain zircon crystals that formed when the ash erupted from a volcano, By Measuring the U—Pb isotope values the timing of eruption can be calculated. However, U—Pb LA-ICPMS or U—Pb Fission track can only be performed in certain circumstances as not all sequences contain bentonites or bentonites that are suitable for U—Pb analysis. The visual analysis of cores or cuttings, at S11a, allows the presence of volcanic ash to be detected. Inductively Coupled Plasma Optical Emission Spectroscopy (ICP-OES) and Mass Spectrometry (MS) performed at S24b can provide indications of the abundance of zircons by using zirconium (Zr) concentrations as a proxy for zircon content.

Another procedure that can be used to link time with a position of the sample extracted from the one or more cores is cyclostratigraphy, at S33. Cyclostratigraphy is the study of astronomically forced cycles within sedimentary depositions. Orbital tuning involves the process of adjusting the time scale of a geologic record so that the observed fluctuations correspond to the Milankovitch cycles in the Earth's orbital motion. Because changes in the Earth's orbit affect the amount and distribution of sunlight the Earth receives, such changes are expected to introduce periodic climate changes on time scales of 20-100 kyr. Long records of sedimentation record such variations and by combining this knowledge with other means of chronostratigraphic control (e.g. magnetostratigraphy, stable isotopes, radiometric age dates, biostratigraphy) it is possible to adjust the timing of features in the geologic record to match orbital theory. This potentially improves the data accuracy. Fourier analysis of sedimentological data such as bed thickness and continually acquired high resolution hand held XRF or MagS data can be used to provide a means to achieve this adjustment of the geologic record within a core.

Another procedure that can be used to link time with a position of the sample from the one or more cores or cuttings includes interpretation of $\delta_{13}C_{org}$ and/or $\delta_{13}C_{carb}$, as shown at point "N" in FIG. 2 that links S27 in FIG. 2 to the Chronostratigraphy Workflow. $\delta^{13}C_{carb}$ reflects changes in dissolved inorganic carbon (DIC) whereas $\delta^{13}C_{org}$ reflects changes in preserved organic carbon (OC). $\delta^{13}C_{carb}$ has average value of approximately 0‰ whereas $\delta C_{org}$ has average value of approximately −25‰. The offset results from kinetic fractionation during photosynthesis. Both can indicate primary productivity and burial rates but can be influenced by different factors. Under normal circumstances, both are correlative and in parallel because there is no change to isotopic fractionation. Since these two variables reflect global changes influenced by the carbon cycle, changes in their values within sediment can provide a way to define chronostratigraphic correlations. In one embodiment, in order to carry out $\delta^{13}C_{org}$ analysis, TOC values obtained from S26a need to be greater than 0.2 weight %. In one embodiment, in order to carry out $\delta^{13}C_{carb}$ analysis, carbonate values, determined either directly at S24a or by element proxy, need to be over 50 weight %.

Another procedure that can be used to link time with a position of the sample from the core includes performing Rhenium-Osmium (Re—OS) chronology procedure, at S34. Re—Os includes the determination of absolute age using Re—OS geochronology (based on the beta decay of the isotope $^{187}$Re to $^{187}$Os). Re—Os may only be performed in certain circumstances. The method includes determining whether the amount of total organic carbon (TOC) or pyrite is equal to or greater than a certain threshold (1.5%), at S35. If the amount of TOC or pyrite is equal to or greater than 1.5%, then the Re—OS chronology or dating procedure, at S34 can be employed. If not, the Re—OS procedure at S34 is not employed for dating. The amount of TOC and Pyrite are determined from, respectively, TOC measurement performed at S26a and (Q)XRD at S24a, as shown at point "M".

All the above dating procedures provide an absolute age of surfaces in a well-bore by analysis of the cores or cuttings and by extension, the age of the stratigraphic layers in the rock formation from which the cores or cuttings are extracted.

The next step is to integrate two or more of the dating procedures (e.g., PMAG, biostratigraphy, interpretation of $\delta_{13}C_{org}$ and/or $\delta_{13}C_{carb}$, U—Pb zircon dating in bentonite, cyclostratigraphy, and/or Re—OS) that are found applicable or relevant to the study sequence in the Chronostratigraphic Workflow. One method used to integrate and test the chronostratigraphic data is by performing a graphic correlation, at S36. Graphic correlation is a conventional procedure used for understanding chronostratigraphic data.

Figure 12:
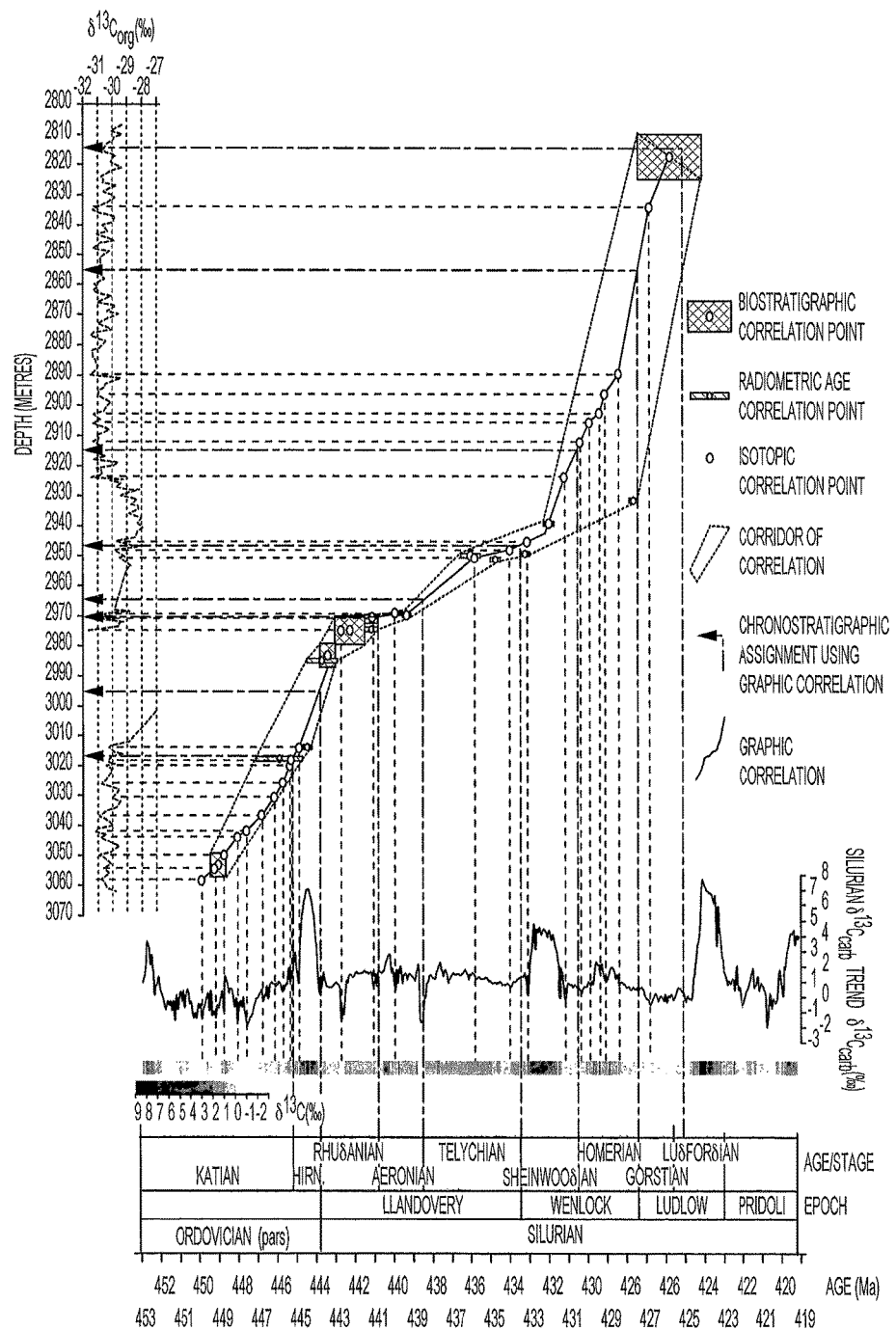
FIG. 12 is an example of a graphic correlation methodology. The two-dimensional plot links chronostratigraphic data from a well (vertical axis) with a composite time scale based on biostratigraphy calibrated to absolute time (horizontal axis). Thin black lines link well data with the composite time scale. The tunnel of correlation (purple area surrounding correlation relationship line) is based on ranges of biostratigraphic data and radiometric ages. The correlation tunnel provides bounding limits in which additional non-unique stratigraphic data can be correlated.

FIG. 12 is an example of a graphic correlation wherein dating procedures are linked and cross referenced. The graphic correlation method is capable of establishing fine time zones with definite boundaries that can be traced over wide geographic areas. The technique involves a graphic plot on a simple two-axis graph. A standard reference section (e.g., geologic time scale) is plotted on the horizontal axis and the geologic section (or core) is plotted on the vertical axis. The plot is based, firstly, on the total stratigraphic range of fossils (biostratigraphy) contained in both sections, and visibly displays the best time correlation between the two sections (geologic section and standard reference section). The graphic method of correlation uses a chronologic scale which differs from both the absolute and relative geochronologic time scales. This new scale can be quantified and used as an accurate measure to subdivide the rock column into high resolution stratigraphic time slices (composite stratigraphic units) with definite boundaries for local and regional correlations. In the present case, the graphic correlation procedure at S36 is used to link two or more of the above dating procedures together and cross reference them in order to ensure they are in the best case scenario and ensure no discrepancies between the results obtained from each method employed. As it can be appreciated, the greater the number of dating procedures that are employed, the greater the degree of cross-referencing and thus the higher confidence level can be established with respect to the graphic correlation as a whole.

A result of graphic correlation, at S36, is obtaining the accumulation rate at S37. In other words, the accumulation rate at S37 is determined using the graphic correlation, at S36. A product of the graphic correlation is the creation of accumulation rate plots in a single section, as shown in FIG. 12. Because high TOC mudrocks only form under slow accumulation rate conditions, the accumulation plots are one of the factors, when combined with data from the Geochemical Workflow, that can be used for determining the potential for high TOC accumulation in a single location.

In addition to the graphic correlation methodology that is done on single well-bores, at S36, well correlations between data from a plurality of wells (two or more wells) can also be constructed, at S38. This procedure uses the available chronostratigraphic data, chemostratigraphic data, lithostratigraphic data in two or more well-bores to correlate surfaces between study wells. These surfaces are interpreted as representing the same time plane in each study well, i.e., they are isochronous surfaces and bound packages of strata that are isochronous.

The interpreted time surfaces from well correlations (e.g., from two or more wells) are then fed back into the graphic correlation, at S36, and the results from the graphic correlation, at S36, are used to test the well correlation, at S38, in an iterative manner. The iterative process ends when as much of the various data sets as possible are honored, crossing between interpreted time surfaces are reduced (ideally, but not essentially, to zero), and the proposed well correlation, at S38, and the graphic correlation, at S36, is deemed to be geologically viable. At this point the chronostratigraphic correlation is completed, at S39.

The chronostratigraphy result, at S39, may not provide a full picture of the history of the deposition in a basin. The full history of the deposition of the basin may be best achieved by inputting all available data into a sequence stratigraphic model, at S40, Sequence stratigraphy procedure, at S40, includes dividing rocks into packages that can be used to interpret changes in base level (which in turn is linked to seal level) in the basin through time. The sequence stratigraphy model at S40 seeks to explain sediment layers in terms of variations in sediment supply and variation in a rate of change in accommodation space (often associated with changes in relative sea level).

Figure 13:
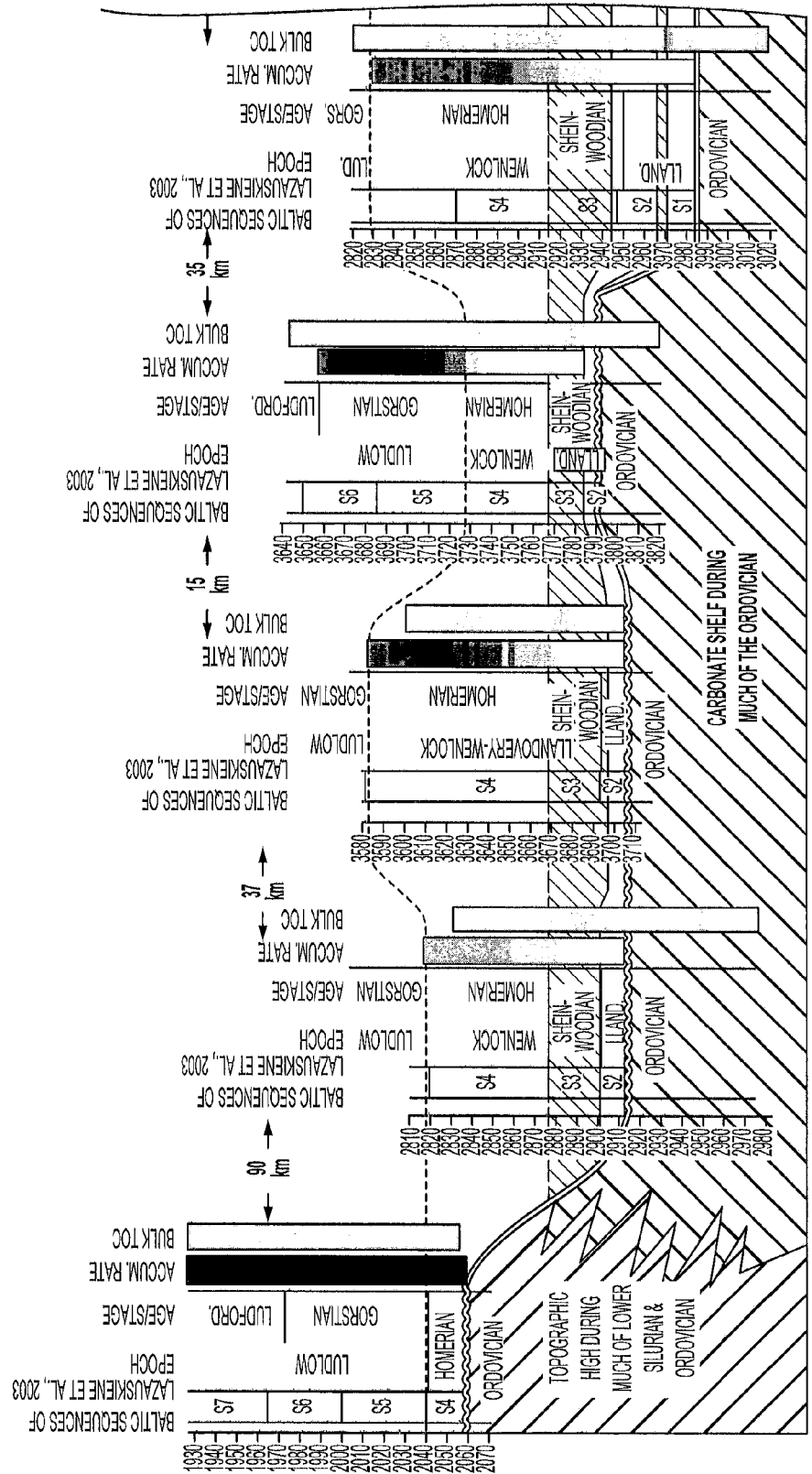
FIG. 13 is a diagram showing a well correlation with accumulation rates derived from a graphic correlation, and a spatial distribution of a set of wells that have been correlated to each other using a graphic correlation and a composite geologic time scale, according to an embodiment of the present invention.
Figure 13:
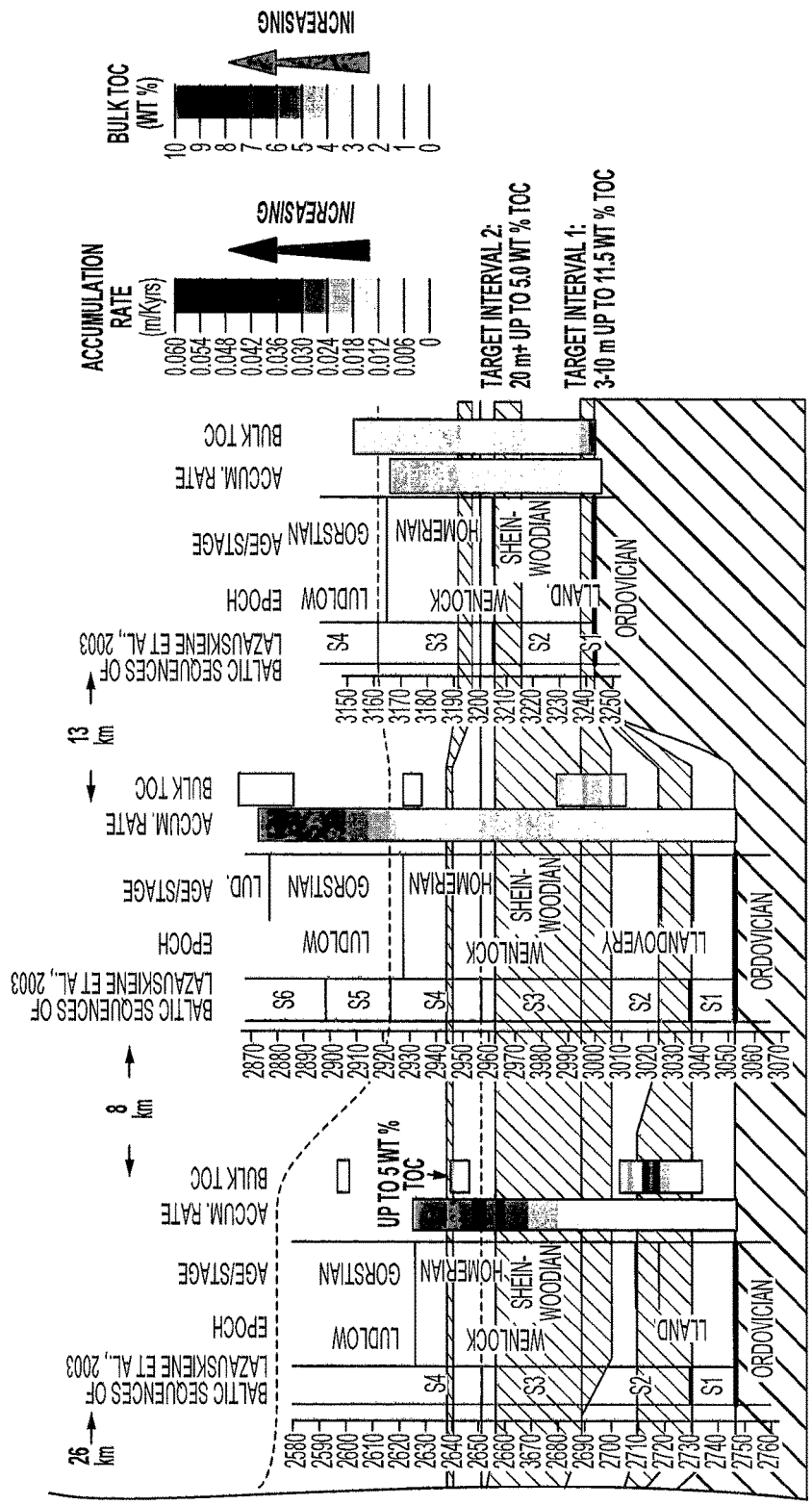

Results obtained from core descriptions at S11a in FIG. 1, the Dilution/Provenance at S24 in FIG. 2, the Redox at S26 in FIG. 2, and Production at S22 in FIG. 2 can also be input into the well correlation procedure S38, as shown through point "P" and "Q", in a manner similar to that shown for accumulation rates on FIG. 13.

Other input data such as core description, chemostratigraphy proxies and magnetic susceptibility results along with other results from point "P" and point "Q", at S41, can be integrated with the chronostratigraphy result, at S39, and input into the sequence stratigraphy, at S40.

The output "B" from the Chronostratigraphic Workflow is a series of isochronous slices of strata that can be correlated between well-bores. By looking at the changes in data obtained from the Geochemical Workflow, the changes in productivity, dilution and accumulation for each isochronous slice between the well-bores can be assessed. The importance of this product is that this enables any data gathered from a single well-bore to be compared to the equivalent data obtained from time equivalent sediments in any other well-bore.

FIG. 13 is a diagram showing a well correlation at S38 with accumulation rates at S37 (FIG. 3) displayed, according to an embodiment of the present invention. FIG. 13 shows the temporal changes in accumulation rates (at S37 in FIG. 3), within a series of wells. Other factors derived from the work flows can also be represented, as shown in FIG. 13. TOC can be input into the well correlation, at S38. In other words, as it can also be appreciated, the diagram in FIG. 13 illustrates a set of wells that are correlated to each other using a graphic correlation, at S36, and a composite geologic time scale. This allows the viewer to determine the impact of accumulation rate on the preservation of organic matter (expressed as TOC) through geologic time.

In order to progress the workflow and provide the geologist a tool to make predictive recommendations on the next best location to place a well, the spatial distribution of the wells, now and, more importantly at the time of sediment deposition needs to be known. As can be appreciated, the wells in FIG. 13 are implied to fall in a straight line, whereas in reality to fully utilize the work flow they need to be placed in their geographic locations in order to understand temporal and 3-dimensional lateral variations in any selected variable.

Figure 4:
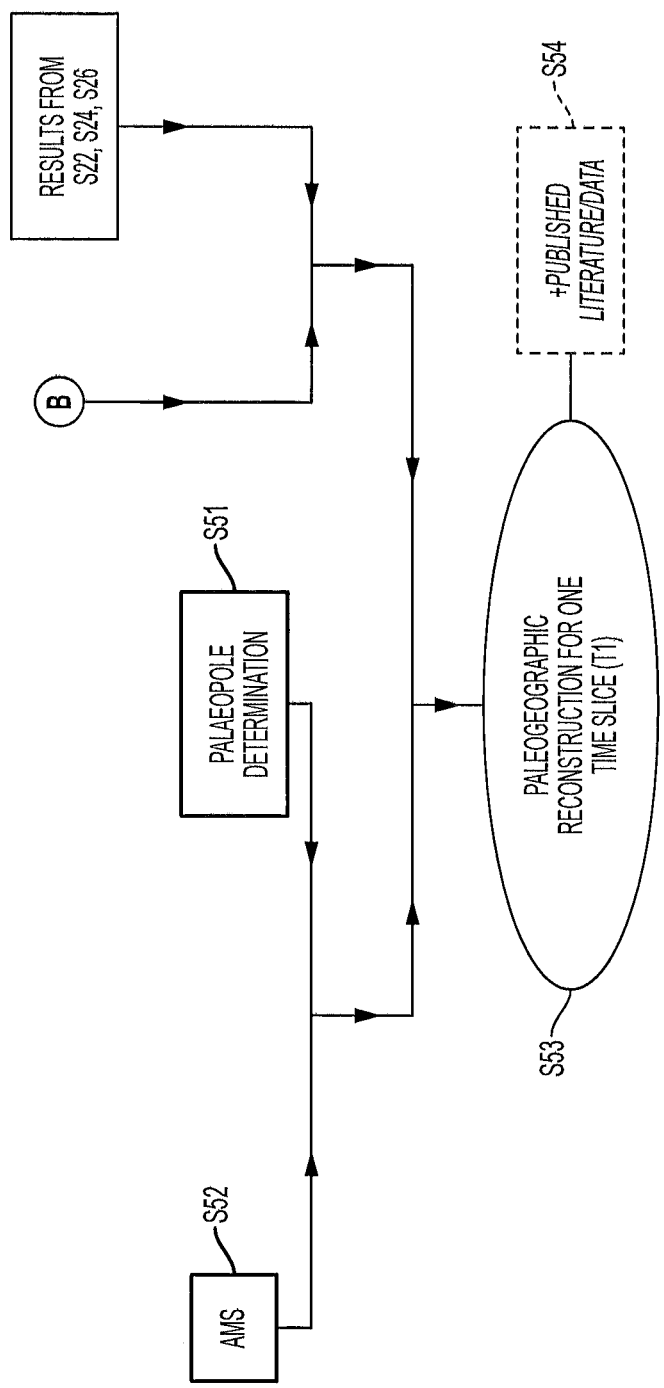
FIG. 4 is a flow chart showing an integration of a dilution model, a redox model, a productivity model, a palaeopole model and an Anisotropic Magnetic Susceptibility (AMS) model to perform a palaeogeographic reconstruction, according to one embodiment of the present invention.

FIG. 4 is a flow chart showing an interpretation and integration of results method, according to an embodiment of the present invention. The overall result of the chronostratigraphy, at S39, integrated with the sequence stratigraphy (sequence stratigraphic model), at S40, and any other input or data, at S41, can be input at point "B" in FIG. 4. The input "B" is a layering of time slices or time periods (as described above and shown in on embodiment FIG. 13) and the results from S22, S24 and/or S26 (Geochemical workflow) together with Anisotropic Magnetic Susceptibility (AMS), at S52, and palaeopole determination, at S51, are used to generate a palaeogeographic reconstruction, at S53, for each time slice or each time period. By producing a palaeogeographic reconstruction for time slices 1-N (N being the number of time slices) and noticing how the variables change in each time slice, it is possible to create the predictive mode, as will be described further with respect to FIG. 5 in the below paragraphs.

Anisotropic Magnetic Susceptibility (AMS) at S52 can be used to interpret the direction in which sediments were transported. The magnetic susceptibility of a rock reflects the degree to which the rock will respond to an applied magnetic field, which is controlled by mineralogy. If a fabric is introduced to a rock during it deposition by water flowing in one direction, the magnetic susceptibility will be different in different directions within the rock, i.e. it will be anisotropic. Measuring the AMS provides insight into water flow direction, which in turn may help in deducing the direction of a coastline or sediment input locations.

In another embodiment of the workflow, the magnetic properties of a core plug may be used to locate where the parent core and therefore the well-bore was located on the earth's surface when the sediment was deposited (at a time of sediment deposition). Palaeomagnetism is used to generate palaeomagnetic poles for tectonic blocks (upon which the well(s) under investigation is/are located) at different epochs, in order to assemble them in Apparent Polar Wander Path (APWP) tracks. Apparent polar wander (APW) is the supposed movement of the Earth's palaeo-magnetic poles relative to a continent while considering that the continent being studied is fixed in position. APW is typically depicted on the present-day latitude-longitude map as a path connecting the locations of geomagnetic poles, inferred at distinct times using palaeomagnetic techniques. Palaeomagnetic poles have the same value at each observing locality on the basis of the Geocentric Axial Dipole (GAD) model. Thus, palaeomagnetic poles can be used to compare palaeomagnetic results from widely separated localities. APWP tracks represent the motion of a plate relative to a fixed point (palaeomagnetic pole). The usual pattern observed consists of long, gently curved segments linked by short, sharply curved segments. Those respectively correspond to time intervals of constant plate motion versus changing plate motion. Fossil magnetization in rocks is used in locating the palaeomagnetic pole. At the time of formation, rocks conserve the direction of the magnetic field. The inclination vector (Im) and declination vector (Dm) are preserved, and therefore the palaeolatitude ($\lambda$p) and palaeolongitude ($\varphi$p) of the pole can be found. The goal of this palaeomagnetic analysis is to assemble poles for the geologic basin of interest and compare them to APWPs for the different continental fragments, which is the first step in reconstructing the palaeogeography.

The processes that result in sediment deposition vary on the earth surface dependent on the climate, which in turn is controlled by the latitude at which the sediments were deposited. Palaeopole analysis as described above provides an indication of palaeolatitude for sediment being analyzed. This is a vital part of developing palaeogeographic models.

Figure 14:
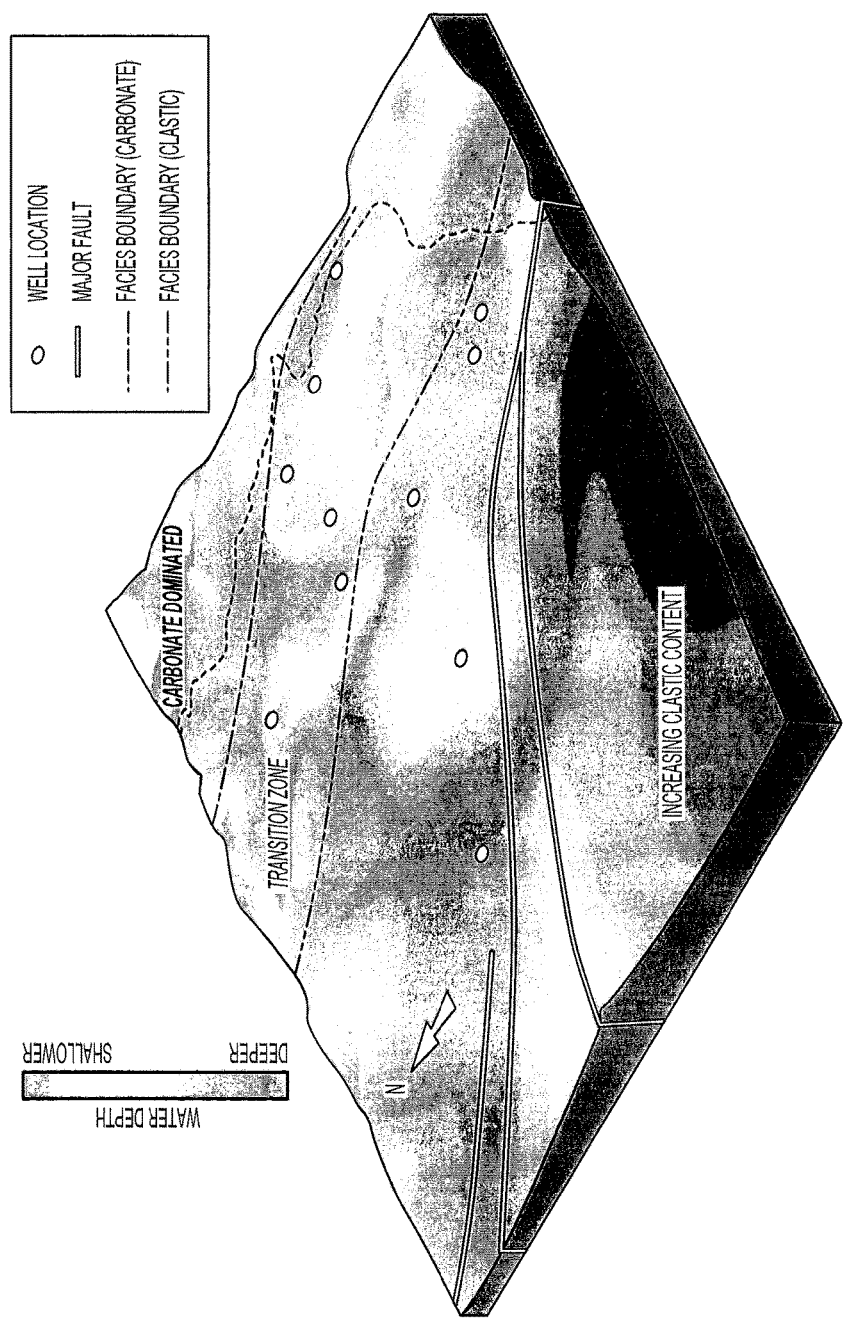
FIG. 14 shows an example of three-dimensional map as a result of Palaeogeographic reconstruction for one time slice, according to an embodiment of the present invention.

FIG. 14 shows an example of three-dimensional map as a result of Palaeogeographic reconstruction for one time slice, according to an embodiment of the present invention. Palaeogeographic Reconstruction is carried out for each time slice (e.g., one time slice is shown in FIG. 14), and the number of time slices can vary from study to study, but dependent on the rate of sampling versus the amount of time encapsulated in the entire study interval. A high sample frequency and large time period will likely result in more time slices than low sample resolution and short time period. In addition to the dilution model, at S24, redox model at S26, and/or productivity model at S22, palaeopole model at S51 and AMS model at S52 that are input to generate a paleaogeographic reconstruction at S53, other published data, at S54, from other sources when available can further be included in the model to provide a more complete palaeogeographic reconstruction at S53.

By looking at the variables obtained from the 'palaeoproductivity' analysis method, at S22, for each time slice, it can be noted how the depositional environment changes laterally in the same time slice. This can provide information on lateral variations in depositional environment within one time slice, where each well-bore analyzed is a control point. By adding AMS at S52 and Palaeopole data at S51 as described above with the results of B (time slices) and the palaeo-productivity analysis at S22, a palaeogeographic reconstruction for one time slice can be generated for time slice T1 (where T1 can be the oldest time slice, for example). By repeating this process for progressively younger time slices T2, T3, etc., the lateral and temporal changes in depositional environment (changing palaeogeography) can be modelled.

Figure 5:
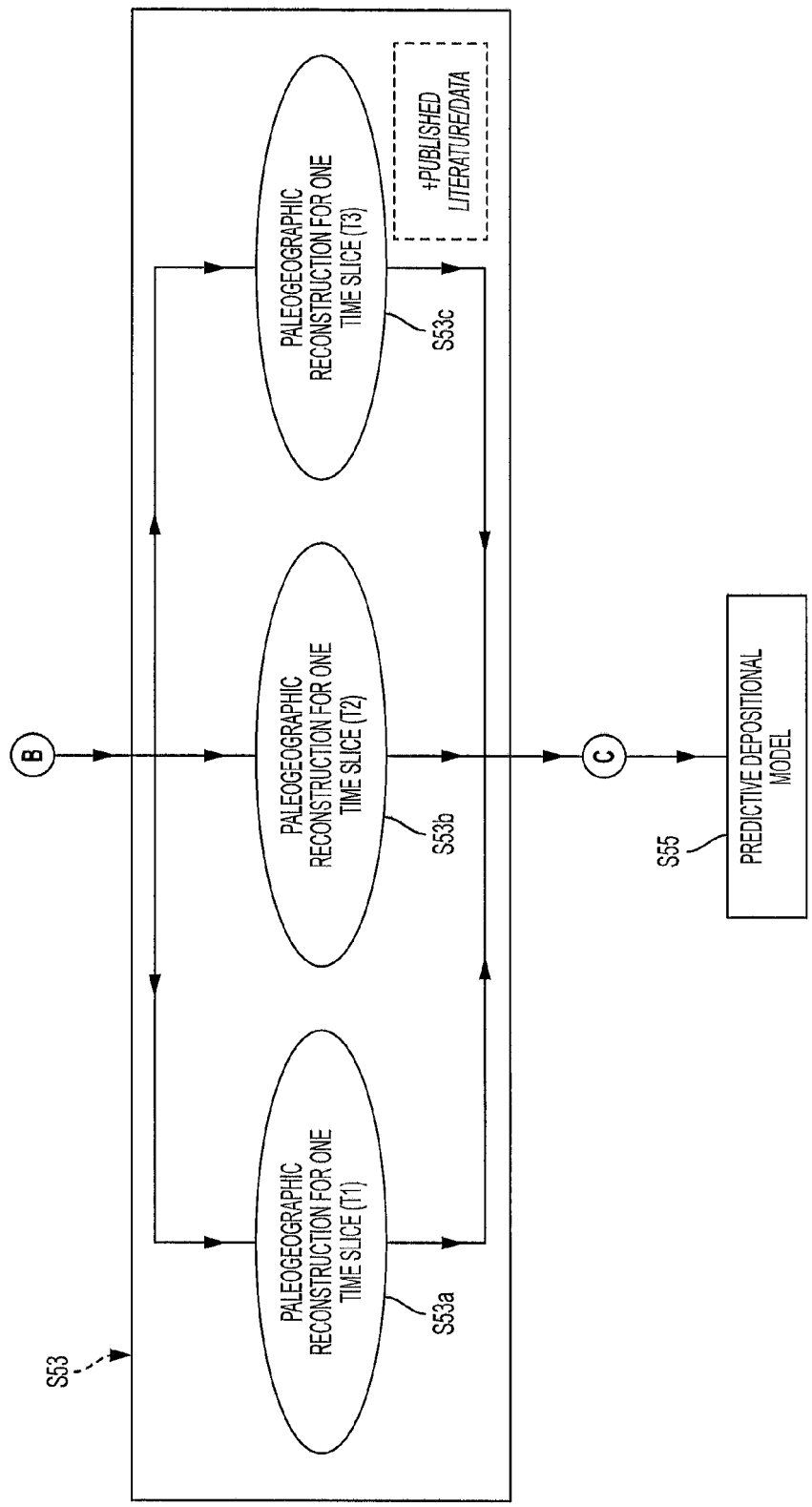
FIG. 5 depicts a flow chart showing a predictive depositional model obtained using palaeogeographic reconstruction at a plurality of time slices, according to an embodiment of the present invention.

FIG. 5 depicts a flow chart showing a predictive depositional model obtained using palaeogeographic reconstruction at a plurality of time slices, according to an embodiment of the present invention. FIG. 5 shows a workflow whereby Palaeogeographic Reconstruction S53 is undertaken for time slice T1 at S53a, then for time slice T2 at S53b, then for time slice T3 at S53c, and so on, until Palaeogeographic reconstructions are completed for all time slices. By building a series of palaeogeographic reconstructions T1-TN (where N is the total number of time slices), the palaeogeographic reconstruction for each time slice (e.g., S53a, S53b or S53c) incorporating the Dilution Model at S24, the Redox Model at S26, the Productivity Model at S22 (i.e., incorporating the geochemical dataset obtained from geochemical analysis method), the AMS at S52 and palaeopole model at S51, the changing nature of the basin can be determined through time, which provides a means to construct a Predictive depositional model, at S55. The result of the palaeogeographic reconstruction at various time slices T1, T2, ..., TN, is used at point "C" to construct a predictive depositional model at S55.

As it can be appreciated, a crude depositional model for a single location can be obtained using the geochemical workflow. A crude basin deposition model (location of coastline and sediment transport direction) can also be obtained from the chronostratigraphic workflow. However, only when the two workflows are combined can a more complete depositional model be constructed that provides insight into the location and areal extent of high TOC shale in a basin. Only by seeing how the basin evolves with time, can an accurate predictive depositional model be generated.

For example, to obtain a basin with a high TOC shale content that is going to be productive, there are a series of conditions that when combined provide a high TOC shale. If one or more of the conditions is not satisfied, this can result in a lesser TOC shale content. For example, if not enough recycling of organic material is not established during deposition in the basin, this can lead to a reduced TOC content in the basin (or reduce the thickness of the TOC interval in the basin). The recycling of organic material is reflected in the productivity model.

Therefore, using this example, the model can be different according to whether or not the recycling is taken into account or not. In one implementation, the model may provide higher productivity leading to thin shales that have accumulated very slowly. When the productivity model is combined with the palaeogeographic reconstruction, this would provide a location where the accumulation rate is low with thin shales. For example, if higher dilution and higher content of sediment is deposited in the basin this may lead to a diluted TOC that is spread over a thick column of sentiment. As a result, this would not lead to high TOC shale and the connectivity between the various organic fragments may be less likely. This would indicate a reduced prospect of capturing the shale gas (for example using fracking).

In addition, there may be a situation where a high TOC gas bearing shales may be present at a time T1 in the rock formation. However, at a later time T2, a million years later, these TOC bearing shales may have relocated to another area. The palaeogeograhic reconstruction provides a physical reconstruction of the basin, whereas the geochemical model, which includes the dilution, the redox and productivity models, provides the information on the geochemistry of the sentiments and water. By combining the palaeogeographic reconstruction with the dilution, redox and productivity models, a more complete depositional model can be achieved. The depositional model provides insight as to where in time (depth) and geographical location higher content of TOC may be available. The depositional model provides a map of a likelihood of finding gas shale or oil in a geographical area and in depth (which reflects time).

In one embodiment, the method or methods described above can be implemented as a series of instructions which can be executed by a computer, the computer having one or more processors or computer processor units (CPUs). For example, the concentration of carbon from organic matter and carbon from carbonate and total organic carbon as a function of depth, as shown in FIG. 9, can be obtained using a computer. The PCA analysis, shown in FIG. 10, or the determination of various plots of concentration of various elements, shown in FIG. 11, can also be implemented using a computer. The computer can also be used to perform the graphic correlation methodology to derive accumulation rates, as depicted, for example in FIG. 12. A computer can also be used to perform a well correlation with accumulation rates derived from a graphic correlation and spatial distribution of a set of wells, as shown, for example in FIG. 13. The computer may also be used to display in a three-dimensional map a result of the Palaeogeographic reconstruction for one time slice, as shown in FIG. 14, or for a plurality of time slices.

As it can be appreciated, the term "computer" is used herein to encompass any type of computing system or device including a personal computer (e.g., a desktop computer, a laptop computer, or any other handheld computing device), or a mainframe computer (e.g., an IBM mainframe), or a supercomputer (e.g., a CRAY computer), or a plurality of networked computers in a distributed computing environment.

For example, the method(s) may be implemented as a software program application which can be stored in a computer readable medium such as hard disks, CDROMs, optical disks, DVDs, magnetic optical disks, RAMs, EPROMs, EEPROMs, magnetic or optical cards, flash cards (e.g., a USB flash card), PCMCIA memory cards, smart cards, or other media.

Alternatively, a portion or the whole software program product can be downloaded from a remote computer or server via a network such as the internet, an ATM network, a wide area network (WAN) or a local area network.

Alternatively, instead or in addition to implementing the method as computer program product(s) (e.g., as software products) embodied in a computer, the method can be implemented as hardware in which for example an application specific integrated circuit (ASIC) can be designed to implement the method.

Various databases can be used which may be, include, or interface to, for example, an OracleTM relational database sold commercially by Oracle Corporation. Other databases, such as Informix™, DB2 (Database 2) or other data storage, including file-based, or query formats, platforms, or resources such as OLAP (On Line Analytical Processing), SQL (Standard Query Language), a SAN (storage area network), Microsoft Access™ or others may also be used, incorporated, or accessed. The database may comprise one or more such databases that reside in one or more physical devices and in one or more physical locations. The database may store a plurality of types of data and/or files and associated data or file descriptions, administrative information, or any other data.

Figure 6:
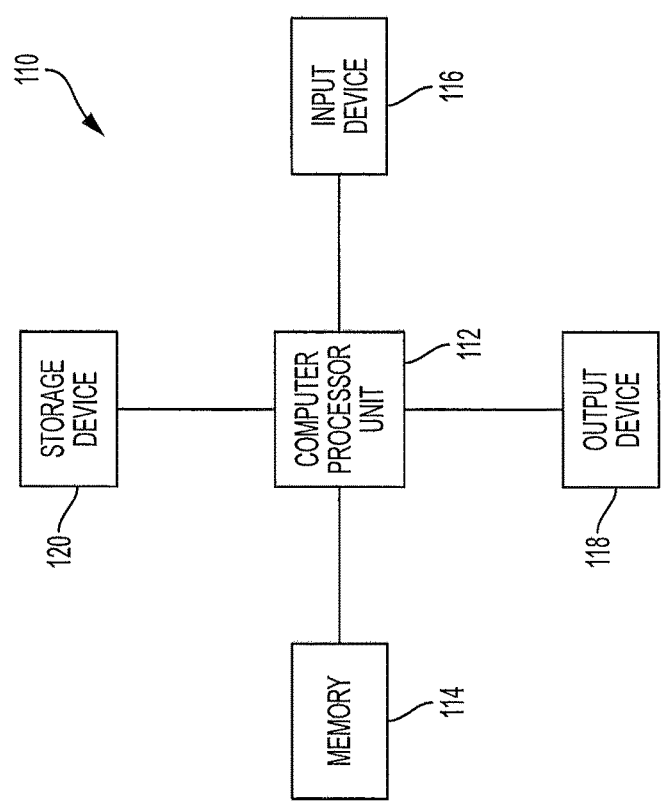
FIG. 6 is a schematic diagram representing a computer system for implementing the methods, according to an embodiment of the present invention.

FIG. 6 is a schematic diagram representing a computer system 110 for implementing the methods, according to an embodiment of the present invention. As shown in FIG. 6, computer system 110 comprises a computer processor unit (e.g., one or more computer processor units) 112 and a memory 114 in communication with the processor 112. The computer system 110 may further include an input device 116 for inputting data (such as keyboard, a mouse or the like) and an output device 118 such as a display device for displaying results of the computation. The computer may further include or be in communication with a storage device 120 for storing data such as, but not limited to, a hard-drive, a network attached storage (NAS) device, a storage area network (SAN), etc. It must be appreciated that the term computer processor unit or processor is used herein to encompass one or more computer processor units. Where reference is made to a processor or computer processor unit that term should be understood to encompass any of these computing arrangements.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

Furthermore, since numerous modifications and changes will readily occur to those of skill in the art, it is not desired to limit the invention to the exact construction and operation described herein. Accordingly, all suitable modifications and equivalents should be considered as falling within the spirit and scope of the invention.

What is claimed is:
1. A method, comprising:
performing a geochemical analysis method to create a geochemical dataset, the geochemical analysis method comprising at least one of: (a) performing a production analysis of organic matter in the past on a sample extracted from a rock formation; (b) determining an amount of sediment dilution in the rock formation; or (c) performing a redox analysis on the sample extracted from the rock formation;
performing a chronostratigraphic method to create a chronostratigraphic dataset, the chronostratigraphic method comprising at least one of: (1) performing a paleomagnetic (PMAG) procedure using a magnetic measuring device to measure changes in direction of magnetism in the rock formation; (2) performing a biostratigraphy procedure to determine time or age of deposition of sediment using flora or fauna dating, or both, if fauna or flora, or both, is found in the rock formation; (3) performing a bentonite analysis procedure; (4) performing a cyclostratigraphy procedure; or (5) performing a Rhenium-Osmium (Re—OS) chronology procedure if an amount of total organic carbon (TOC) or Pyrite determined using the geochemical analysis method is equal to or greater than approximately 1.5%;
measuring changes in preserved organic carbon $\delta^{13}C_{org}$ or changes in dissolved inorganic carbon $\delta^{13}C_{carb}$, or both, to recognize global changes in oceanic dissolved inorganic carbon;
performing a graphic correlation of the chronostratigaphic dataset;
determining a sequence stratigraphic model based on the graphic correlation; and generating a palaeogeographic reconstruction through time by integrating the sequence stratigraphic model with the geochemical dataset to construct a predictive depositional model and determine a location and areal extent of total organic carbon of shale within the rock formation at present day.

2. The method according to claim 1, further comprising determining an accumulation rate of hydrocarbon deposits in the at least one location using the graphic correlation, wherein the accumulation rate provides an indication of a location of carbon deposits in the rock formation.

3. The method according to claim 1, further comprising incorporating the geochemical dataset obtained from the geochemical analysis method at different time periods into the sequence stratigraphic model.

4. The method according to claim 3, further comprising using the geochemical dataset with a palaeopole model and an anisotropic magnetic susceptibility (AMS) model to generate the palaeogeographic reconstruction for each time period.

5. The method according to claim 4, further comprising interpreting a direction of transport of sediments using the anisotropic magnetic susceptibility (AMS) model.

6. The method according to claim 4, further comprising determining water flow direction and direction of coastline or sediment input locations using the anisotropic magnetic susceptibility (AMS) model.

7. The method according to claim 3, further comprising determining a location of a well on earth surface at a time of sediment deposition using paleomagnetism.

8. The method according to claim 4, further comprising generating the palaeogeographic reconstruction at a plurality of time periods using the geochemical dataset, the palaeopole model, the anisotropic magnetic susceptibility (AMS) model, and additional published data from other sources.

9. The method according to claim 1, wherein performing the production analysis of organic matter in the past includes determining a proportion of elements that are present in the rock formation and measuring an amount of carbon in an organic fraction in the rock formation.

10. The method according to claim 1, wherein determining the amount of sediment dilution in the rock formation includes determining a dilution amount of organic material that accumulated in sediments in the rock formation relative to other elements or compounds in the sediments in the rock formation.

11. The method according to claim 10, wherein determining the amount of sediment dilution includes using an X-Ray diffraction mineral model using an X-Ray diffraction apparatus or a Fourier Transform Infrared apparatus, or both.

12. The method according to claim 10, wherein determining the amount of sediment dilution includes using inductively coupled plasma optical emission spectroscopy (ICP-OES) or mass spectrometry (MS), or both, by employing an inductively coupled plasma optical emission spectrometer or a mass spectrometer, or both.

13. The method according to claim 10, wherein determining the amount of sediment dilution includes using magnetic susceptibility by employing a magnetic susceptibility measuring apparatus.

14. The method according to claim 1, wherein performing the redox analysis includes determining proxies that provide information about oxic and anoxic conditions of a water column and a sediment column.

15. The method according to claim 1, wherein performing the redox analysis comprises determining total preserved organic content in the sediments.

16. The method according to claim 1, wherein performing the redox analysis comprises measuring a ratio of pyrite iron to the sum of pyrite iron and reactive iron.

17. The method according to claim 1, wherein performing the redox analysis comprises measuring euxinic condition in a water column.

18. The method according to claim 1, further comprising inputting the geochemical dataset from the geochemical analysis method into a component analysis to identify which of various chemical proxies have geochemical associations.

19. The method according to claim 2, further comprising inputting the accumulation rate into a well correlation procedure.

20. The method according to claim 19, wherein inputting the accumulation rate into the well correlation procedure comprises inputting results of the graphic correlation into a well correlation procedure between two or more well locations.

21. The method according to claim 20, further comprising feeding back results obtained from the well correlation procedure into the graphic correlation.

22. The method according to claim 21, further comprising testing the well correlation procedure iteratively using results from the graphic correlation.

23. The method according to claim 20, further comprising inputting into the well correlation procedure the geochemical dataset.

24. The method according to claim 19, further comprising inputting the accumulation rate into the sequence stratigraphic model.

25. The method according to claim 24, wherein determining the sequence stratigraphic model comprises dividing rocks into packages that are used to interpret changes in base level which are linked to sea level in a given basin through time.

26. The method according to claim 24, further comprising obtaining a series of isochronous slices of strata that are correlated with well bores and assessing changes in the geochemical dataset obtained from the geochemical method including changes in sediment dilution and accumulation for each isochronous slice between two or more well bores.

27. The method according to claim 26, comparing data obtained from one well location to equivalent data from another well location.

28. The method according to claim 24, further comprising integrating the geochemical dataset from the geochemical analysis method, core description, or the magnetic susceptibility, or any combination thereof, with the sequence stratigraphic model.

29. The method according to claim 28, further comprising performing the palaeogeographic reconstruction through time to model temporal changes in a depositional environment by using results of an anisotropic magnetic susceptibility procedure, the geochemical dataset, results from the sequence stratigraphic model, and results from a palaeopole or palaeomagnetic pole determination.

30. The method according to claim 29, further comprising using the palaeomagnetic pole determination to compare palaeomagnetic results from separate geographical locations.

31. The method of claim 1, wherein performing a bentonite analysis comprises performing a uranium-lead (U—Pb), Laser Ablation Inductively Coupled Plasma Mass Spectrometry (LA-ICPMS) or U—Pb fission track analysis, or any combination thereof.

* * * * *